(12) United States Patent
Gevas et al.

(10) Patent No.: US 8,343,930 B2
(45) Date of Patent: Jan. 1, 2013

(54) COMBINATION THERAPY FOR THE TREATMENT OF TUMORS

(75) Inventors: Philip C. Gevas, Key Biscayne, FL (US); Stephen Grimes, Davis, CA (US); Stephen L. Karr, Davis, CA (US); Susan A. Watson, Nottingham (GB); Dov Michaeli, Larkspur, CA (US)

(73) Assignee: Cancer Advances, Inc., Durham, NC (US)

( * ) Notice: Subject to any disclaimer, the term of this patent is extended or adjusted under 35 U.S.C. 154(b) by 0 days.

(21) Appl. No.: 12/693,127

(22) Filed: Jan. 25, 2010

(65) Prior Publication Data

US 2010/0129382 A1 May 27, 2010

Related U.S. Application Data

(63) Continuation of application No. 12/313,969, filed on Nov. 25, 2008, now abandoned, which is a continuation of application No. 09/700,402, filed on May 4, 2001, now abandoned.

(51) Int. Cl.
*A61K 38/00* (2006.01)

(52) U.S. Cl. .................................... 514/19.3

(58) Field of Classification Search .................. None
See application file for complete search history.

(56) References Cited

U.S. PATENT DOCUMENTS

| | | | |
|---|---|---|---|
| 3,391,141 A | 7/1968 | Wissmann | |
| 4,069,313 A | 1/1978 | Woodhour et al. | |
| 4,196,265 A | 4/1980 | Koprowski et al. | |
| 4,201,770 A | 5/1980 | Stevens | |
| 4,302,386 A | 11/1981 | Stevens | |
| 4,384,995 A | 5/1983 | Stevens | |
| 4,526,716 A | 7/1985 | Stevens | |
| 4,565,805 A | 1/1986 | Smirnov | |
| 4,687,759 A | 8/1987 | Martinez et al. | |
| 4,691,006 A | 9/1987 | Stevens | |
| 4,713,366 A | 12/1987 | Stevens | |
| 4,762,913 A | 8/1988 | Stevens | |
| 4,767,842 A | 8/1988 | Stevens | |
| 4,794,103 A | 12/1988 | Bertolini | |
| 4,803,170 A | 2/1989 | Stanton et al. | |
| 4,816,567 A | 3/1989 | Cabilly et al. | |
| 4,840,939 A | 6/1989 | Leveen et al. | |
| 4,894,443 A | 1/1990 | Greenfield et al. | |
| 4,923,819 A | 5/1990 | Fernandez et al. | |
| 4,925,922 A | 5/1990 | Byers et al. | |
| 4,971,792 A | 11/1990 | Steplewski et al. | |
| 4,978,683 A | 12/1990 | Rovati et al. | |
| 4,997,950 A | 3/1991 | Murphy et al. | |
| 5,006,334 A | 4/1991 | Stevens | |
| 5,023,077 A | 6/1991 | Gevas et al. | |
| 5,035,988 A | 7/1991 | Nakamura et al. | |
| 5,055,404 A | 10/1991 | Ueda et al. | |
| 5,110,911 A | 5/1992 | Samuel et al. | |
| 5,120,829 A | 6/1992 | Pierschbacher et al. | |
| 5,162,504 A | 11/1992 | Horoszewisz | |
| 5,164,299 A | 11/1992 | Lambert | |
| 5,242,799 A | 9/1993 | Samuel et al. | |
| 5,256,542 A | 10/1993 | Chang | |
| 5,319,073 A | 6/1994 | Wank | |
| 5,468,494 A * | 11/1995 | Gevas et al. ............. | 424/195.11 |
| 5,484,596 A | 1/1996 | Hanna, Jr. et al. | |
| 5,580,563 A | 12/1996 | Tam et al. | |
| 5,585,474 A | 12/1996 | Iwaki et al. | |
| 5,607,676 A | 3/1997 | Gevas et al. | |
| 5,609,870 A | 3/1997 | Gevas et al. | |
| 5,622,702 A | 4/1997 | Gevas et al. | |
| 5,639,613 A | 6/1997 | Shay et al. | |
| 5,643,735 A | 7/1997 | Yokoi et al. | |
| 5,665,864 A | 9/1997 | Quaranta et al. | |
| 5,665,874 A | 9/1997 | Kuhajda et al. | |
| 5,668,117 A | 9/1997 | Shapiro | |
| 5,683,695 A | 11/1997 | Shen et al. | |
| 5,688,504 A * | 11/1997 | Morgan, Jr. ............. | 424/141.1 |
| 5,688,506 A | 11/1997 | Grimes et al. | |
| 5,698,201 A | 12/1997 | Stevens | |
| 5,703,213 A | 12/1997 | Wands et al. | |
| 5,712,369 A | 1/1998 | Old et al. | |
| 5,723,718 A | 3/1998 | Berens | |
| 5,731,159 A | 3/1998 | Waldman | |
| 5,733,790 A | 3/1998 | Potter et al. | |
| 5,736,146 A | 4/1998 | Cohen et al. | |
| 5,750,119 A | 5/1998 | Srivastava | |
| 5,759,551 A | 6/1998 | Ladd et al. | |
| 5,759,791 A | 6/1998 | Kuhajda et al. | |
| 5,767,242 A | 6/1998 | Zimmerman et al. | |

(Continued)

FOREIGN PATENT DOCUMENTS

EP          0 380 230          11/1994

(Continued)

OTHER PUBLICATIONS

Watson et al Int. J. Cancer vol. 75 p. 873 (Mar. 6, 1998).*
Watson et al Cancer Research vol. 56 p. 880 (1996).*
Beauchamp et al Annals of Surgery vol. 202 p. 303 (1985).*
Abbruzzese et al Cancer Research vol. 49 p. 4057 (1989).*
"Gastrin 17 immunogen Aphton begins combination study," R&D Focus Drug News, IMS World Publications (2000).
Ajani et al., "An Open-Label, Multinational, Multicenter Study of G17DT Vaccination Combined with Cisplatin and 5-Fluorouracil in Patients with Untreated, Advanced Gastric or Gastroesophageal Cancer: The GC4 Study," Cancer. vol. 106, No. 9 pp. 1908-1916 (2006).
Caplin et al., "Targeted radiopeptide therapy: High dose indium-111 octreotide for neuroendocrin tumours," Gastroenterology. vol. 114, Suppl. 1 p. A574 (1998) [Abstract # G2348].
Cole, "Immunoassay of human chorionic gonadotropin, its free subunits, and metabolites," Clinical Chemistry. vol. 43, No. 12 pp. 2233-2243 (1997).
de Jong et al., "Effects of partial liver resection on tumor growth," Journal of Hepatology. vol. 25 pp. 109-121 (1996).

(Continued)

*Primary Examiner* — Sheela J Huff
(74) *Attorney, Agent, or Firm* — Jenkins, Wilson, Taylor & Hunt, P.A.

(57) ABSTRACT

The present invention relates to a combination therapy method for treating gastrin-dependent tumors. The method comprises the immunization of a patient with an anti-gastrin 17 immunogenic composition in combination with the administration of chemotherapeutic agents such as 5-fluorouracil and leucovorin.

16 Claims, 3 Drawing Sheets

U.S. PATENT DOCUMENTS

| | | | |
|---|---|---|---|
| 5,770,576 A * | 6/1998 | Morozov et al. | 514/19 |
| 5,785,970 A * | 7/1998 | Gevas et al. | 424/184.1 |
| 5,786,213 A | 7/1998 | Singh et al. | |
| 5,788,964 A | 8/1998 | Baral et al. | |
| 5,827,691 A | 10/1998 | Iwaki et al. | |
| 5,843,446 A | 12/1998 | Ladd et al. | |
| 5,866,128 A | 2/1999 | Gevas et al. | |
| 5,866,617 A * | 2/1999 | Hausheer et al. | 514/772 |
| 5,869,045 A | 2/1999 | Hellstrom et al. | |
| 5,869,058 A | 2/1999 | Cohen et al. | |
| 5,879,898 A | 3/1999 | Tarin et al. | |
| 5,932,412 A | 8/1999 | Dillner et al. | |
| 5,955,504 A * | 9/1999 | Wechter et al. | 514/568 |
| 5,981,167 A | 11/1999 | Taremi et al. | |
| 6,132,720 A | 10/2000 | Grimes et al. | |
| 6,169,173 B1 | 1/2001 | Wank | |
| 6,180,370 B1 | 1/2001 | Queen et al. | |
| 6,187,536 B1 | 2/2001 | Weinberg et al. | |
| 6,191,290 B1 | 2/2001 | Safavy | |
| 6,251,581 B1 | 6/2001 | Ullman et al. | |
| 6,303,123 B1 | 10/2001 | Grimes et al. | |
| 6,320,022 B1 | 11/2001 | Cutitta et al. | |
| 6,359,114 B1 | 3/2002 | Grimes et al. | |
| 6,391,299 B1 | 5/2002 | Blackburn et al. | |
| 6,444,207 B1 | 9/2002 | Shoemaker et al. | |
| 6,472,506 B1 | 10/2002 | Moreau et al. | |
| 6,548,066 B1 * | 4/2003 | Michaeli et al. | 424/185.1 |
| 6,565,813 B1 | 5/2003 | Garyantes | |
| 6,613,530 B1 | 9/2003 | Wienhues et al. | |
| 6,627,196 B1 | 9/2003 | Baughman et al. | |
| 6,639,055 B1 | 10/2003 | Carter et al. | |
| 6,689,869 B2 | 2/2004 | Waldmann et al. | |
| 6,696,262 B2 | 2/2004 | Harkonen | |
| 6,699,974 B2 | 3/2004 | Ono et al. | |
| 6,780,969 B2 | 8/2004 | Wang | |
| 6,815,414 B2 | 11/2004 | Chowers et al. | |
| 6,835,543 B2 | 12/2004 | Saitoh et al. | |
| 6,861,510 B1 | 3/2005 | Gevas et al. | |
| 6,872,543 B1 | 3/2005 | Sipponen et al. | |
| 7,074,761 B1 | 7/2006 | Hinuma et al. | |
| 7,192,582 B2 | 3/2007 | Hudson et al. | |
| RE39,586 E | 4/2007 | Dagan | |
| 7,235,376 B2 | 6/2007 | Grimes et al. | |
| 7,300,918 B2 | 11/2007 | Rath | |
| 7,438,907 B2 | 10/2008 | Schuurman et al. | |
| 7,662,926 B2 | 2/2010 | Chan et al. | |
| 7,964,371 B2 | 6/2011 | Grimes et al. | |
| 8,013,115 B1 | 9/2011 | Garric et al. | |
| 8,158,128 B2 | 4/2012 | Grimes | |
| 2001/0020005 A1 | 9/2001 | Chowers et al. | |
| 2002/0058040 A1 | 5/2002 | Grimes et al. | |
| 2002/0095028 A1 | 7/2002 | Grimes et al. | |
| 2003/0021786 A1 | 1/2003 | Gevas et al. | |
| 2003/0049698 A1 | 3/2003 | Wang | |
| 2003/0068326 A1 | 4/2003 | Gevas et al. | |
| 2003/0082643 A1 | 5/2003 | Hudson et al. | |
| 2003/0086941 A1 | 5/2003 | Michaeli et al. | |
| 2003/0091574 A1 | 5/2003 | Gevas et al. | |
| 2003/0138860 A1 | 7/2003 | Robertson et al. | |
| 2003/0232399 A1 | 12/2003 | Robertson et al. | |
| 2004/0001842 A1 | 1/2004 | Michaeli et al. | |
| 2004/0063164 A1 | 4/2004 | Lassalle | |
| 2004/0266682 A1 | 12/2004 | Cruz | |
| 2005/0014138 A1 | 1/2005 | Rath | |
| 2005/0025770 A1 | 2/2005 | Gevas et al. | |
| 2005/0069966 A1 | 3/2005 | Grimes et al. | |
| 2005/0169979 A1 | 8/2005 | Michaeli et al. | |
| 2005/0187152 A1 | 8/2005 | Gevas et al. | |
| 2006/0020119 A1 | 1/2006 | Grimes et al. | |
| 2006/0039911 A1 | 2/2006 | Gevas et al. | |
| 2006/0140962 A1 | 6/2006 | Gevas et al. | |
| 2007/0031511 A1 | 2/2007 | Baldwin et al. | |
| 2007/0065454 A1 | 3/2007 | Michaeli et al. | |
| 2007/0066809 A1 | 3/2007 | Grimes | |
| 2007/0082043 A1 | 4/2007 | Michaeli et al. | |
| 2007/0248608 A1 | 10/2007 | Grimes et al. | |
| 2007/0249005 A1 | 10/2007 | Grimes et al. | |
| 2009/0004200 A1 | 1/2009 | Gevas et al. | |
| 2009/0191232 A1 | 7/2009 | Gevas et al. | |
| 2011/0117108 A1 | 5/2011 | Gevas et al. | |

FOREIGN PATENT DOCUMENTS

| | | |
|---|---|---|
| EP | 0 755 683 | 1/1997 |
| EP | 0 818 680 | 1/1998 |
| EP | 1 129 724 | 9/2001 |
| EP | 1 579 863 | 9/2005 |
| JP | 06107564 A | 4/1994 |
| WO | WO 90/08774 * | 8/1990 |
| WO | WO94/00590 | 1/1994 |
| WO | WO94/07530 | 4/1994 |
| WO | WO95/04544 | 2/1995 |
| WO | WO95/13297 | 5/1995 |
| WO | WO95/21380 | 8/1995 |
| WO | WO96/15456 | 5/1996 |
| WO | WO97/28821 | 8/1997 |
| WO | WO97/38584 | 10/1997 |
| WO | WO98/31393 | 7/1998 |
| WO | WO98/51337 | 11/1998 |
| WO | WO99/19353 | 4/1999 |
| WO | WO99/59612 | 11/1999 |
| WO | WO99/59628 | 11/1999 |
| WO | WO99/59631 | 11/1999 |
| WO | WO99/65513 | 12/1999 |
| WO | WO00/67035 | 11/2000 |
| WO | WO01/13114 | 2/2001 |
| WO | WO01/34192 | 5/2001 |
| WO | WO01/77685 | 10/2001 |
| WO | WO02/39123 | 5/2002 |
| WO | WO02/076499 | 10/2002 |
| WO | WO03/005955 | 1/2003 |
| WO | WO2004/023148 | 3/2004 |
| WO | WO2004/088326 | 10/2004 |
| WO | WO2005/095459 | 10/2005 |
| WO | WO2006/008649 | 1/2006 |
| WO | WO2006/016275 | 2/2006 |
| WO | WO2006/032980 | 3/2006 |
| WO | WO2007/062531 | 6/2007 |

OTHER PUBLICATIONS

De Magistris, L., and Rehfeld, J.F., "A Simple Enzymatic Procedure for Radioimmunochemical Quantitation of the Large Molecular Forms of Gastrin and Cholecystokinin," Analytical Biochemistry. vol. 102 pp. 126-133 (1980).

Deed of Letters Patent corresponding to Australian Patent Application No. 2004225437 dated Aug. 26, 2010.

Demeester et al., "Patterns of Gastroesophageal Reflux in Health and Disease," Ann. Surg. vol. 184, No. 4 pp. 459-469 (1976).

de Weerth et al., "Human Pancreatic Cancer Cell Lines Express the CCKB Receptor," Hepato-Gastroenterology. vol. 46 pp. 472-478 (1999).

de Weerth et al., "Human Pancreatic Cancer Cell Lines Express the $CCK_B$/Gastrin Receptor," Gastroenterology. vol. 106, No. 4 p. A289 (1994) [Abstract].

Del Valle et al., "Progastrin and Its Glycine-Extended Post-translational Processing Intermediates in Human Gastrointestinal Tissues," Gastroenterology. vol. 92, No. 6 pp. 1908-1912 (1987).

Dethloff et al., "Inhibition of Gastrin-Stimulated Cell Proliferation by the CCK-B/gastrin Receptor Ligand CI-988," Food and Chemical Toxicology. vol. 37 pp. 105-110 (1999).

Dickinson, "Relationship of Gastrin Processing to Colon Cancer," Gastroenterology. vol. 109, No. 4 pp. 1384-1388 (1995).

Dickinson, C.J., and Yamada, T., "Gastrin-amidating Enzyme in the Porcine Pituitary and Antrum," The Journal of Biological Chemistry. vol. 266, No. 1 pp. 334-338 (1991).

Dockray, "Immunochemical Studies on Big Gastrin Using NH2-Terminal Specific Antisera," Regulatory Peptides. vol. 1 pp. 169-186 (1980).

Dockray, G.J., and Taylor, I.L., "Heptadecapeptide Gastrin: Measurement in Blood by Specific Radioimmunoassay," Gastroenterology. vol. 71, No. 6 pp. 971-977 (1976).

Dockray, G.J., and Walsh, J.H., "Amino-Terminal Gastrin Fragment in Serum of Zollinger-Ellison Syndrome Patients," Gastroenterology. vol. 68, No. 2 pp. 222-230 (1975).

Dockray et al., "Gastric Endocrine Cells: Gene Expression, Processing, and Targeting of Active Products," Physiological Review. vol. 76, No. 3 pp. 767-798 (1996).

Dockray et al., "Immunochemical studies on big gastrin using $NH_2$-terminal specific antiserums," Regulatory Peptides. vol. 1, No. 3 pp. 169-186 (1980). Chemical Abstracts vol. 94 pp. 506-507 (1981) [Abstract #94:119200w].

Dockray et al., "The Gastrins: Their Production and Biological Activities," Ann. Rv. Physiol. vol. 63 pp. 119-139 (2001).

Douziech et al. "Growth Effects of Regulatory Peptides and Intracellular Signaling Routes in Human Pancreatic Cancer Cell Lines," Endocrine. vol. 9, No. 2 pp. 171-183 (1998).

Du et al. "Biochip as a potential platform of serological interferon α2b antibody assay," Journal of Biotechnology. vol. 106, No. 1 pp. 87-100 (2003).

Dufresne et al., "Cholecystokinin and Gastrin Receptors," Physiol. Rev. vol. 86 pp. 805-847 (2006).

Edgington, "Biotech Vaccines' Problematic Promise," Bio/Technology. vol. 10 pp. 763-766 (1992).

Edkins, "On the Chemical Mechanism of Gastric Secretion," Proceedings of the Royal Society of London. Series B, Containing Papers of a Biological Character. vol. 76, No. 510 p. 376 (1905).

Edkins, "The Chemical Mechanism of Gastric Secretion," J. Physiol. vol. 34, Nos. 1-2 pp. 133-144 (1906).

Erlichman et al., "A Randomized Trial of Fluorouracil and Colonic Acid in Patients With Metastatic Colorectal Carcinoma," Journal of Clinical Oncology. vol. 6 pp. 469-475 (1988).

Evans, "Chemotherapy in Advanced Non-Small Cell Lung Cancer," $37^{th}$ Annual Meeting of the American Society of Clinical Oncology, Day 1, May 22, 2001, meeting report published by Medscape.

Ezzell, "Cancer 'Vaccines': An Idea Whose Time Has Come?" The Journal of NIH Research. vol. 7 pp. 46-49 (1995).

Fennerty, "Updated on Barrett's Esophagus" Digestive Diseases Week, May 22, 2001, meeting report published by Medscape, www.medscape.com, 6 pages.

Festen et al., "Effect of Oral Omeprazole on Serum Gastrin and Serum Pepsinogen I Levels," Gastroenterology. vol. 87, No. 5 pp. 1030-1034 (1984).

Feurle et al. "The Role of CCK and its Analogues in the Organogenesis of the Fetal Rat Pancreas," Pancreas. vol. 10, No. 3 pp. 281-286 (1995).

Fields, "Preparation of Antipeptide Antibodies: Introduction to Peptide Synthesis," Current Protocols in Molecular Biology. 11.15.1-11.15.9 (2002).

Finley et al., "Expression of the Gastrin Gene in the Normal Human Colon and Colorectal Adenocarcinoma," Cancer Research. vol. 53 pp. 2919-2926 (1993).

Fornai et al., "Cholecystokinin CCK2 receptors mediate the peptide's inhibitory actions on the contractile activity of human distal colon via the nitric oxide pathway," British Journal of Pharmacology. vol. 151 pp. 1246-1253 (2007).

Fourmy et al., "Relationship of CCK/gastrin-receptor binding to amylase release in dog pancreatic acini," Regulatory Peptides. vol. 10 pp. 57-68 (1984).

Fraser, "Effects of Antibodies to Luteinizing Hormone Releasing Hormone on Reproductive Functions in Rodents," Immunization With Hormones in Reproduction Research. Nieschlag ed. North Holland Publishing. pp. 107-117 (1975).

Freston, "Long-Term Acid Control and Proton Pump Inhibitors: Interactions and Safety Issues in Perspective," American Journal of Gastroenterology. vol. 92, No. 4 pp. 51S-57S (1997).

Frucht et al., "Characterization of Functional Receptors for Gastrointestinal Hormones on Human Colon Cancer Cells," Cancer Research. vol. 52, No. 5 pp. 1114-1122 (1992).

Gil-Delgado et al., "Prospective Phase II Trial of Irinotecan, 5-Fluorouracil, and Leucovorin in Combinations as Salvage Therapy for Advanced Colorectal Cancer," American Journal of Clinical Oncology. vol. 24, No. 1 pp. 101-105 (2001).

Gilliam, A.D., and Watson, S.A., "G17DT: an antigastrin immunogen for the treatment of gastrointestinal malignancy," Expert Opinion Biol. Ther. vol. 7, No. 3 pp. 397-404 (2007).

Gilliam et al., "A phase II study of G17DT in gastric carcinoma," EJSO. vol. 30 pp. 536-543 (2004).

Gilliam et al., "Randomized, double blind, placebo-controlled, multi-centre, group-sequential trial of G17DT for patients with advanced pancreatic cancer unsuitable or unwilling to take chemotherapy," Journal of Clinical Oncology. ASCO Annual Meeting Proceedings. vol. 22, No. 14S p. 2511 (2004) [Abstract].

Gocyk et al. "*Helicobacter pylori*, gastrin and cyclooxygenase-2 in lung cancer," Med. Sci. Monit. vol. 6, No. 6 pp. 1085-1092 (2000).

Goetze, J.P., and Rehfeld, J.F., "Impact of Assay Epitope Specificity in Gastrinoma Diagnosis," Clinical Chemistry. vol. 49, No. 2 pp. 333-334 (2003).

Goletti et al. "Resection of Liver Gastrinoma Leading to Persistent Eugastrinemia," Eur. J. Surgery. vol. 158 pp. 55-57 (1992).

Grabowska, A., and Watson, S.A., "Downregulation of the Gastrin Gene Using Small Interfering RNA," Regulatory Peptides. vol. 122, No. 1 p. 46 (2004) [Abstract # A150].

Gregory, R.A., and Tracy, H.J., "Isolation of Two Gastrins from Human Antral Mucosa," Nature. vol. 209, No. 5023 p. 583 (1966).

Grider, J.R., and Makhlouf, G.M., "Distinct receptors for cholecystokinin and gastrin on muscle cells of stomach and gallbladder," Am. J. Physiol. vol. 259 pp. G184-G190 (1990).

Gupta, J.R., and Siber, G.R., "Adjuvants for human vaccines—current status, problems and future prospects," Vaccine. vol. 13, No. 14 pp. 1263-1276 (1995).

Gura, T., "Systems for Identifying New Drugs Are Often Faulty," Science. vol. 278, No. 5340 pp. 1041-1042 (1997).

Gutman et al., "Accelerated Growth of Human Colon Cancer Cells in Nude Mice Undergoing Liver Regeneration," Invasion and Metastasis. vol. 14, Nos. 1-6 pp. 362-371 (1994-95).

Haigh et al. "Gastrin Induces Proliferation in Barrett's Metaplasia Through Activation of the CCK2 Receptor," Gastroenterology. vol. 124 pp. 615-625 (2003).

Halter et al., "Evaluation of a Monoclonal Anti-Gastrin Antibody as a Tool for Immunoneutralization of Gastrin During Omeprazole Treatment in the Rat," Gastroenterology. vol. 96, No. 5, Part 2 p. A194 (1989).

Hananel et al., "Hepatic Resection for Colorectal Liver Metastasis," The American Surgeon. vol. 61, No. 5 pp. 444-447 (1995).

Harlow, E., and Lane, D., Antibodies: A Laboratory Manual, Cold Spring Harbor Laboratory Press. Cold Spring Harbor, NY. pp. 7-13, 23-26, 142-143, 148-149 (1988).

Harlow, E., and Lane, D., Antibodies: A Laboratory Manual. Cold Spring Harbor Laboratory Press. Cold Spring Harbor, NY. pp. 555-556, 559, 561, 578-581, and 591-593 (1988).

Harris et al., "An Antiapoptotic Role for Gastrin and the Gastrin/CCK-2 Receptor in Barrett's Esophagus," Cancer Research. vol. 64, No. 6 pp. 1915-1919 (2004).

Harris et al., "The Biological and Therapeutic Importance of Gastrin Gene Expression in Pancreatic Adenocarcinomas," Cancer Research. vol. 64 pp. 5624-5631 (2004).

Harrison et al. "The Effect of the Gastrin Receptor Antagonist Proglumide on Survival in Gastric Carcinoma," Cancer. vol. 66, No. 7 pp. 1449-1452 (1990).

He, A.R., and Marshall, J.L., "Clinical experiences with G17DT in gastrointestinal malignancies," Expert Rev. Anticancer Ther. vol. 6, No. 4 pp. 487-492 (2006) [Abstract].

He et al., "Biological Activity and Ferric Ion Binding of Fragments of Glycine-Extended Gastrin," Biochemistry. vol. 43, No. 37 pp. 11853-11861 (2004).

Heinemann et al., "Cellular Elimination of 2',2'-Diflourodeoxycytidine 5'-Triphosphate: A Mechanism of Self-Potentiation," Cancer Research. vol. 52 pp. 533-539 (1992).

Helander et al., "Immunohistochemical and localization of gastrin/CCK-B receptors in the dog and guinea-pig stomach," Acta Physiologica Scandinavica. vol. 159, No. 4 pp. 313-320 (1997).

Hellmich et al., "Human Colorectal Cancers Express a Constitutively Active Cholecystokinin-B/Gastrin Receptor That Stimulates Cell Growth," The Journal of Biological Chemistry. vol. 275, No. 41 pp. 32122-32128 (2000).

Henwood et al., "Expression of gastrin in developing gastric adenocarcinoma," British Journal of Surgery. vol. 88 pp. 564-568 (2001).

Herbert et al. (Eds.) "The Dictionary of Immunology," 3rd Ed. Academic Press, London, p. 41 (1995).

Herget et al., "Cholecystokinin Stimulates Ca$^{2+}$ Mobilization and Clonal Growth in Small Cell Lung Cancer through CCK$_A$ and CCK$_B$/ Gastrin Receptors," Annals New York Academy of Sciences. vol. 713, pp. 283-297 (1994).
Hoosein et al., "Antiproliferative Effects of Gastrin Receptor Antagonists and Antibodies to Gastrin on Human Colon Carcinoma Cell Lines," Cancer Research. vol. 48 pp. 7179-7183 (1988).
Hoosein et al., "Evidence for Autocrine Growth Stimulation of Cultured Colon Tumor Cells by a Gastrin/Cholecystokinin-like Peptide," Experimental Cell Research. vol. 186, No. 1 pp. 15-21 (1990).
Houghten et al., "Relative Importance of Position and Individual Amino Acid Residues in Peptide Antigen-Antibody Interactions: Implications in the Mechanism of Antigenic Drift and Antigenic Shift," Vaccines. vol. 86 pp. 21-25 (1986).
Hsi, "A Practical Approach for Evaluating New Antibodies in the Clinical Immunohistochemistry Laboratory," Arch. Pathol. Lab. Med. vol. 125 pp. 289-294 (2001).
Huang et al., "Termination of DNA Synthesis by 9-β-D-Arabinofuranosyl-2-fluroadenine," The Journal of Biological Chemistry. vol. 265, No. 27 pp. 16617-16625 (1990).
Hughes et al., "Development of a class of selective cholecystokinin type B receptor antagonists having potent anxiolytic activity," PNAS. vol. 87 pp. 6728-6732 (1990).
Hughes et al., "Therapy with Gastrin Antibody in the Zollinger-Ellison Syndrome," Digestive Diseases. vol. 21 pp. 201-204 (1976).
Ichikawa et al., "Distinct effects of tetragastrin, histamine, and CCh on rat gastric mucin synthesis and contribution of NO," Am. J. Physiol. vol. 274, No. 1 pp. G138-G146 (1998).
Ikeda et al., "Preliminary report of tumor metastasis during liver regeneration after hepatic resection in rats," European Journal of Surgical Oncology. vol. 21, No. 2 pp. 188-190 (1995).
International Preliminary Examination Report corresponding to International Patent Application No. PCT/US1999/010734 dated Dec. 9, 2000.
International Preliminary Examination Report corresponding to International Patent Application No. PCT/US2002/008756 dated May 26, 2006.
International Preliminary Examination Report corresponding to International Patent Application No. PCT/US2002/021768 dated Feb. 9, 2004.
International Preliminary Report on Patentability corresponding to International Patent Application No. PCT/US2004/009666 dated Jan. 19, 2006.
International Preliminary Report on Patentability corresponding to International Patent Application No. PCT/US2005/002793 dated Aug. 7, 2007.
International Preliminary Report on Patentability corresponding to International Patent Application No. PCT/US2005/010532 dated Nov. 3, 2006.
International Search Report corresponding to International Patent Application No. PCT/US1990/000520 dated May 21, 1990.
International Search Report corresponding to International Patent Application No. PCT/US1999/010751 dated Oct. 19, 1999.
International Search Report corresponding to International Patent Application No. PCT/US2004/009666 dated Nov. 8, 2004.
International Search Report corresponding to International Patent Application No. PCT/US2005/010532 dated Feb. 8, 2006.
Issued Patent corresponding to Australian Patent Application No. 2005228897 dated Mar. 25, 2010.
Iwanaga et al., "Immunocytochemical Localization of the Different Gastrin Forms in the *Pyloric antrum*," Biomedical Research. vol. 1 pp. 316-320 (1980).
Iwao et al., "Effects of Omeprazole and Lansoprazole on Fasting and Postprandial Serum Gastrin and Serum Pepsinogen A and C," Hepato-Gastroenterology. vol. 42 pp. 677-682 (1995).
Iwase et al., "Regulation of Growth of Human Gastric Cancer by Gastrin and Glycine-Extended Progastrin," Gastroenterology. vol. 113 pp. 782-790 (1997).
Jaffe et al., "Gastrin resistance following immunization to the C-terminal tetrapeptide amide of gastrin," Surgery. vol. 69, No. 2 pp. 232-237 (1971).

Jaffe et al., "Inhibition of Endogenous Gastrin Activity by Antibodies to the Carboxyl-Terminal Tetrapeptide Amide of Gastrin," Gastroenterology. vol. 58, No. 2 pp. 151-156 (1970).
Jaffe et al., "Inhibition of gastrin activity by incubation with antibodies to the C-terminal tetrapeptide of gastrin," Surgery. vol. 65, No. 4 pp. 633-639 (1969).
Jain, "Barriers to Drug Delivery in Solid Tumors," Scientific American. vol. 171, No. 1 pp. 58-65 (1994).
Janeway et al. "Immunobiology: The Immune System in Health and Disease," Fourth Edition, Elsevier Science Ltd./Garland Publishing, New York, NY p. 544 (1999).
Johnson, "New Aspects of the Trophic Action of Gastrointestinal Hormones," Gastroenterology. vol. 72, No. 4, Part 2 pp. 788-792 (1977).
Johnson et al, "Ornithine Decarboxylase in Large Bowel Mucosa: Regulation by Gastrin, Secretin and EGF," Journal of Physiology and Pharmacology. vol. 43, No. 1 pp. 33-41 (1992).
Jonsson, A., and Dockray, G.J., "Immunohistochemical localization to pyloric antral G cells of peptides derived from porcine preprogastrin," Regulatory Peptides. vol. 8 pp. 283-290 (1984).
Joshi, S.N., and Gardner, J.D., "Gastrin and Colon Cancer: A Unifying Hypothesis," Digestive Diseases. vol. 14 pp. 334-344 (1996).
Justin et al., "Gastric Acid Suppression Using Anti-Gastrin-17 Antibodies Produced by a Gastrin Immunogen, Gastrimmune, in an In Vivo Pig Model," Gastroenterology. vol. 108, No. 4 p. A125 (1995) [Abstract].
Kaiser, "First Pass at Cancer Genome Reveals Complex Landscape," Science. vol. 313 p. 1370 (2006).
Kameyama et al., "Adjuvant Chemo-Endocrine Chemotherapy with Gastrin Antagonist After Resection of Liver Metastasis in Colorectal Cancer," Japanese Journal of Cancer and Chemotherapy. vol. 21, No. 13 pp. 2169-2171 (1994) [Abstract].
Katoh et al., "Malignant Zollinger-Ellison Syndrome. Stabilizing of Liver Metastasis After Gastrectomy with Resection of Primary Tumor," The American Surgeon. vol. 56, No. 6 pp. 360-363 (1990)
Kaufmann et al., "Cholecystokinin B-type receptor signaling is involved in human pancreatic cancer cell growth," Neuropeptides. vol. 31, No. 6 pp. 573-583 (1997).
Kelley et al., "Antitumor Activity of a Monoclonal Antibody Directed Against Gastrin-Releasing Peptide in Patients with Small Cell Lung Cancer," Chest. vol. 112 pp. 256-261 (1997).
Kelly et al., "Pathophysiology of GI Tract and Liver: Expression of progastrin-derived peptides and gastrin receptors in a panel of gastrointestinal carcinoma cell lines," Journal of Gastroenterology and Hepatology. vol. 13 pp. 208-214 (1998).
Kipriyanov, S.M., and Little, M., "Generation of Recombinant Antibodies," Molecular Biotechnology. vol. 12 pp. 173-201 (1999).
Kobori et al., "Growth Responses of Rat Stomach Cancer Cells to Gastro-Entero-Pancreatic Hormones," International Journal of Cancer. vol. 30, No. 1 pp. 65-67 (1982).
Kochman et al, "Post-Translational Processing of Gastrin in Neoplastic Human Colonic Tissues," Biochemical and Biophysical Research Communications. vol. 189, No. 2 pp. 1165-1169 (1992).
Koelz, "Treatment of Reflux Esophagitis with H2-Blockers. Antacids and Prokinetic Drugs. An Analysis of Randomized Clinical Trials," Scandinavian Journal of Gastroenterology. Supplement 156 pp. 25-36 (1989).
Koh et al., "Gastrin Deficiency Results in Altered Gastric Differentiation and Decreased Colonic Proliferation in Mice," Gastroenterology. vol. 113, No. 3 pp. 1015-1025 (1997).
Koh et al., "Glycine-Extended Gastrin Promotes the Growth of a Human Hepatoma Cell Line," Gastroenterology. vol. 110, No. 4 p. A1089 (1996) [Abstract].
Koh et al., "Glycine-Extended Gastrin Promotes the Growth of Lung Cancer," Cancer Research. vol. 64 pp. 196-201 (2004).
Kohler et al., "Continuous cultures of fused cells secreting antibody of predefined specificity," Nature. vol. 256 pp. 495-497 (1975).
Kopin et al. "Expression, cloning and characterization of the canine parietal cell gastrin receptor," PNAS. vol. 89 pp. 3605-3609 (1992).
Kothary, P.C., and Lvinik, A., "NH2-Terminal of Gastrin-17 in Duodenal Ulcer Disease: Identification of Progastrin-17," Biochemical and Biophysical Research Communications. vol. 146, No. 2 pp. 884-888 (1987).

Kothary et al., "Identification of gastrin molecular variants in gastrinoma syndrome," Regulatory Peptides. vol. 17 pp. 71-84. (1987).

Kovacs et al., "Gastrin is a Major Mediator of the Gastric Phase of Acid Secretion in Dogs: Proof by Monoclonal Antibody Neutralization," Gastroenterology. vol. 97 pp. 1406-1413 (1989).

Kovacs et al., "Gastrin Partially Mediates Insulin-Induced Acid Secretion in Dogs," Peptides. vol. 17, No. 4 pp. 583-587 (1996).

Kovacs et al. "Inhibition of sham feeding-stimulated acid secretion in dogs by immunoneutralization of gastrin," Am. J. Physiol. vol. 273 (Gastrointest. Liver Physiol. 36) p. G399-G403 (1997).

Kuipers et al., "Atrophic Gastritis and *Helicobacter pylori* Infection in Patients with Reflux Esophagitis Treated with Omeprazole or Fundoplication," New England Journal of Medicine. vol. 334, No. 16 pp. 1018-1022 (1996).

Kuipers et al., "The Efficacy and Safety of Long-term Omeprazole Treatment for Gastroesophageal Reflux Disease," Gastroenterology. vol. 118, No. 4 pp. 795-798 (2000).

Kusyk et al., "Stimulation of growth of a colon cancer cell line by gastrin," Am. J. Physiol. vol. 251 pp. G597-G601 (1986).

Lamberts et al., "Effects of Very Long (up to 10 years) Proton Pump Blockade on Human Gastric Mucosa," Digestion. vol. 64 pp. 205-213 (2001).

Lamers, C.B.H.W., and Jansen, J.B.M.J., "Role of Gastrin of the Cholecystokinin in Tumours of the Gastrointestinal Tract," Eur. J. Cancer Clin. Oncol. vol. 24, No. 2 pp. 267-273 (1988).

Lamote, J., and Willems, G., "Stimulating effect of pentagastrin on cancer cell proliferation kinetics in chemically induced colon cancer in rats," Regulatory Peptides. vol. 20 pp. 1-9 (1988).

Landis et al., "Cancer Statistics, 1998" CA—A Cancer Journal for Clinicians. vol. 48, No. 1 pp. 6-30 (1998).

Larsson, "Histochemistry of Gastrin Cells," Neurohistochemistry: Modern Methods and Applications. Alan R. Liss, Inc., pp. 527-567 (1986).

Larsson, L., and Rehfeld, J.F., "Characterization of Antral Gastrin Cells With Region-Specific Antisera," The Journal of Histochemistry and Cytochemistry. vol. 25, No. 12 pp. 1317-1321 (1977).

Laurie, S.A., and Kris, M.G., "Single-Agent Docetaxel (Taxotere) in the Treatment of Advanced Non-Small-Cell Lung Cancer: Clinical Concepts and Commentary," Clinical Lung Cancer. vol. 1, Suppl 1 pp. S5-S9 (2000).

Lawrence et al., "Radiosensitization of Pancreatic Cancer Cells by 2', 2'-Difluoro-2'-Deoxycytidine," Int. J. Radiation Oncology Biol. Phys. vol. 34, No. 4 pp. 867-872 (1996).

Le Meuth et al., "Differential Expression of A- and B-Subtypes of Cholecystokinin/Gastrin-Receptors in the Developing Calf Pancreas," Endocrinology. vol. 133, No. 3 pp. 1182-1191 (1993).

Ledda-Columbano et al., "Compensatory Regeneration, Mitogen-Induced Liver Growth, and Multistage Chemical Carcinogenesis," Environmental Health Perspectives. vol. 101, No. 5 pp. 163-168 (1993).

Lee et al., "The Human Brain Cholecystokinin-B/Gastrin Receptor," The Journal of Biological Chemistry. vol. 268, No. 11 pp. 8164-8169 (1993).

Leith et al., "Effects of Partial Hepatectomy on Growth Characteristics and Hypoxic Fractions of Xenografted DLD-2 Human Colon Cancers," Radiation Research. vol. 123, No. 2 pp. 263-268 (1992).

Li et al., "Induction of growth inhibition and apoptosis in pancreatic cancer cells by auristatin-PE and gemcitabine," International Journal of Molecular Medicine. vol. 3 pp. 647-653 (1999).

MacKenzie et al., "Development of a Radioligand Binding Assay to Characterise Gastrin Receptors in the Human Gastrointestinal Tract," Gut. vol. 38, Suppl. 1 p. A37 (1996) [Abstract # T146].

Mahood et al., "Inhibition of Fluorouracil Stomatitis by Oral Cryotherapy," Journal of Clinical Oncology. vol. 9 pp. 449-452 (1991).

Makishima et al., "Active Immunization Against Gastrin-17 With an N-Terminal Derived Immunogen Inhibits Gastric and Duodenal Lesions in Rats," Gastroenterology. vol. 106, No. 4, Part. 2 p. A824 (1994) [Abstract].

Makishima et al., "Inhibition of Gastrin-17 Stimulated Acid Secretion Thorugh Active Immunization in Rats," FASEB Journal. vol. 8, Nos. 4-5 p. A92 (1994) [Abstract #535].

Mandair et al., "Cholecystokinin Receptors in Human Pancreatic Cancer Cell Lines," European Journal of Cancer. vol. 34, No. 9 pp. 1455-1459 (1998).

Marino et al., "Expression and Post-translational Processing of Gastrin in Heterologous Endocrine Cells," The Journal of Biological Chemistry. vol. 266, No. 10 pp. 6133-6136 (1991).

Martin et al. "Selection of Trypsin of 2 Sublines of Rat Cancer Cells Forming Progressive or Regressive Tumors," Int. J. Cancer. vol. 32 pp. 623-627 (1983).

Masseyeff, R.F., and Ferrua, B., "The Art of Assay Design in Heterologous Enzyme Immunoassay," International symposium on immunoenzymatic techniques. vol. 2 pp. 139-155 (1983).

Matsumoto et al. "Gastrin receptor characterization: affinity cross-linking of the gastric receptor on canine gastric parietal cell" Am J. Physiol. vol. 252 p. G143-G147 (1987).

McCloy et al., "Pathophysiological Effects of Long-Term Acid Suppression in Man," Digestive Diseases and Sciences. vol. 40, No. 2 pp. 96S-120S [Supplement] (1995).

McGregor et al., "Trophic Effects of Gastrin on Colorectal Neoplasms in the Rat," Ann. Surg. vol. 195, No. 2 pp. 219-223 (1982).

McRae et al., "Role of Gastrin and Gastrin Receptors in the Growth of Human Colon Carcinoma Cells," The Journal of Cell Biology. vol. 103, No. 5, Part 2 p. 22a (1986) [Abstract # 74].

McWilliams et al., "Antibodies raised against the extracellular tail of the CCKB/gastrin receptor inhibit gastrin-stimulated signalling," Regulatory Peptides. vol. 99, Nos. 2-3 pp. 157-161 (2001).

McWilliams et al., "Coexpression of gastrin and gastrin-receptors (CCK-B and CCK-B) in gastrointestinal tumour cell lines," Gut. vol. 42 pp. 795-798 (1998).

Miyake, "A Truncated Isoform of Human CCK-B/Gastrin Receptor Generated by Alternative Usage of a Novel Exon," Biochemical and Biohysical Research Communications. vol. 208, No. 1 pp. 230-237 (1995).

Mizutani et al., "Promotion of hepatic metastases by liver resection in the rat," British J. Cancer. vol. 65, No. 6 pp. 794-797 (1992).

Moertel, C.G., "Chemotherapy for Colorectal Cancer," The New England Journal of Medicine. vol. 330, No. 16 pp. 1136-1142 (1994).

Moody et al., "GRP Receptors Are Present in Non Small Cell Lung Cancer Cells," Journal of Cellular Biochemistry Supplement. vol. 24 pp. 247-256 (1996).

Moroder, L., and Wunsch, E., "Gastrins and Cholecystokinins: Chemical and Immunological Aspects," Gastrin and Cholecystokinin. Chemistry, physiology and pharmacology. (Ed. J. Bali et al.) Elsevier Science Publishers B.V. pp. 21-32 (1987).

MSNBC News Services, "Mixed results on new cancer drug," Nov. 9, 2000 (4 pages).

Mu et al., "Monoclonal antibody to the gastrin receptor on parietal cells recognizes a 78-kDa protein," PNAS. vol. 84 pp. 2698-2702 (1987).

Mulholland et al., "Elevated Gastric Acid Secretion in Patients with Barrett's Metaplastic Epithelium," Digestive Diseases and Sciences. vol. 34, No. 9 pp. 1329-1334 (1989).

Nakata et al., "Cloning and Characterization of Gastrin Receptor From ECL Carcinoid Tumor of Mastomys Natalensis," Biochemical and Biophysical Research Communications. vol. 187, No. 2 pp. 1151-1157 (1992).

Narayan et al., "Characterization of gastrin binding to colonic mucosal membranes of guinea pigs," Molecular and Cellular Biochemistry. vol. 112 pp. 163-171 (1992).

National Institutes of Health Publication No. 99-4546, "Barrett's Esophagus," National Digestive Diseases Information Clearinghouse. pp. 1-3 (May 1999).

NCBI Accession No. NP 795344. Fornai et al., "Cholecystokinin CCK2 receptors mediate the peptide's inhibitory actions on the contractile activity of human distal colon via the nitric oxide pathway," British Journal of Pharmacology. vol. 151, No. 8 pp. 1246-1253 (2007).

Negre et al., "Autocrine Stimulation of AR4-2J Rat Pancreatic Tumor Cell Growth by Glycine-Extended Gastrin," Int. J. Cancer. vol. 66, No. 5 pp. 653-658 (1996).

Nemeth et al., "Development of a sequence-specific radioimmunoassay by using N-terminal gastrin 1-13 antibody," Chemical Abstracts. vol. 98 p. 495 (1983) [Abstract # 98:51653w].

Nemeth et al., "Identification of progastrin derived peptides in colorectal carcinoma extracts," Gut. vol. 34 pp. 90-95 (1993).
Notice of Acceptance corresponding to Australian Patent Application No. 2004225437 dated Apr. 29, 2010.
Notice of Acceptance corresponding to Australian Patent Application No. 2005228897 dated Nov. 25, 2009.
Notice of Allowance corresponding to Japanese Patent Application No. 2006-509465 dated Jan. 18, 2011.
Notice of Allowance corresponding to U.S. Appl. No. 10/813,336 dated May 15, 2006.
Notice of Allowance corresponding to U.S. Appl. No. 10/813,336 dated Oct. 3, 2006.
Notice of Allowance corresponding to U.S. Appl. No. 10/813,336 dated Feb. 7, 2007.
Notice of Allowance corresponding to U.S. Appl. No. 11/800,889 dated Feb. 7, 2011.
Ochiai et al., "Growth-Promoting Effect of Gastrin on Human Gastric Carcinoma Cell Line TMK-1," Japan Journal of Cancer Research. vol. 76 pp. 1064-1071 (1985).
Official Action corresponding to Australian Patent Application No. 199940798 dated Jul. 13, 2001.
Official Action corresponding to Australian Patent Application No. 199940798 dated Jul. 24, 2003.
Official Action corresponding to Australian Patent Application No. 2004225437 dated Dec. 15, 2009.
Official Action corresponding to Australian Patent Application No. 2005286164 dated Feb. 14, 2011.
Official Action corresponding to Canadian Patent Application No. 2,450,898 dated May 28, 2010.
Official Action corresponding to Canadian Patent Application No. 2,520,010 dated Aug. 17, 2009.
Official Action corresponding to Canadian Patent Application No. 2,520,010 dated Nov. 1, 2010.
Official Action corresponding to Canadian Patent Application No. 2,561,405 dated Jul. 31, 2009.
Official Action corresponding to Canadian Patent Application No. 2,561,405 dated Nov. 3, 2010.
Official Action corresponding to Canadian Patent Application No. 2,580,965 dated Sep. 30, 2010.
Official Action corresponding to Chinese Patent Application No. 200580017341.9 dated Jun. 19, 2009.
Official Action corresponding to Chinese Patent Application No. 200580036710.9 dated Feb. 24, 2011.
Official Action corresponding to European Patent Application No. 02 721 529.2-2107 dated Sep. 23, 2004.
Official Action corresponding to European Patent Application No. 04 758 568.2-2404 dated Jul. 17, 2007.
Official Action corresponding to European Patent Application No. 05 730 336.4-1222 dated Apr. 27, 2007.
Official Action corresponding to European Patent Application No. 05 784 499.5-2406 dated Jul. 8, 2010.
Official Action corresponding to European Patent Application No. 99 924 252.2-2107 dated Jul. 4, 2003.
Official Action corresponding to European Patent Application No. 99 924 252.2-2107 dated Mar. 31, 2004.
Official Action corresponding to Indian Patent Application No. 2441/CHENP/2005 dated Jul. 24, 2007.
Official Action corresponding to Indian Patent Application No. 6318/DELNP/2006/707 dated Jul. 5, 2010.
Official Action corresponding to Israeli Patent Application No. 182012 dated Dec. 31, 2009.
Official Action corresponding to Japanese Patent Application No. 2006-509465 dated Oct. 21, 2009.
Official Action corresponding to Japanese Patent Application No. 2006-509465 dated Aug. 26, 2010.
Official Action corresponding to Japanese Patent Application No. 2007-506474 dated Jun. 1, 2010.
Official Action corresponding to U.S. Appl. No. 08/219,773 dated Oct. 19, 1994.
Official Action corresponding to U.S. Appl. No. 08/285,984 dated Feb. 7, 1995.
Official Action corresponding to U.S. Appl. No. 08/465,917 dated Aug. 12, 1996.
Official Action corresponding to U.S. Appl. No. 10/104,607 dated Mar. 29, 2005.
Official Action corresponding to U.S. Appl. No. 10/104,607 dated Nov. 21, 2005.
Official Action corresponding to U.S. Appl. No. 10/192,257 dated Sep. 21, 2005.
Official Action corresponding to U.S. Appl. No. 10/762,226 dated Dec. 27, 2006.
Official Action corresponding to U.S. Appl. No. 10/813,336 dated Jun. 23, 2005.
Official Action corresponding to U.S. Appl. No. 10/813,336 dated Oct. 20, 2005.
Official Action corresponding to U.S. Appl. No. 11/093,724 dated Nov. 25, 2005.
Official Action corresponding to U.S. Appl. No. 11/093,724 dated Feb. 6, 2006.
Official Action corresponding to U.S. Appl. No. 11/252,904 dated Jan. 8, 2009.
Official Action corresponding to U.S. Appl. No. 11/252,904 dated Oct. 26, 2009.
Official Action corresponding to U.S. Appl. No. 11/252,904 dated Jul. 20, 2010.
Official Action corresponding to U.S. Appl. No. 11/663,126 dated Jun. 22, 2009.
Official Action corresponding to U.S. Appl. No. 11/663,126 dated Nov. 25, 2009.
Official Action corresponding to U.S. Appl. No. 11/663,126 dated Jun. 2, 2010.
Official Action corresponding to U.S. Appl. No. 11/499,261 dated Mar. 15, 2007.
Official Action corresponding to U.S. Appl. No. 11/499,261 dated Nov. 30, 2007.
Official Action corresponding to U.S. Appl. No. 11/499,261 dated Sep. 24, 2008.
Official Action corresponding to U.S. Appl. No. 11/499,261 dated May 14, 2009.
Official Action corresponding to U.S. Appl. No. 11/499,261 dated Nov. 15, 2010.
Official Action corresponding to U.S. Appl. No. 11/499,261 dated Apr. 26, 2011.
Official Action corresponding to U.S. Appl. No. 11/800,889 dated Oct. 2, 2009.
Official Action corresponding to U.S. Appl. No. 11/800,889 dated Feb. 18, 2010.
Official Action corresponding to U.S. Appl. No. 11/800,889 dated Jun. 23, 2010.
Official Action corresponding to U.S. Appl. No. 12/221,956 dated May 28, 2010.
Official Action corresponding to U.S. Appl. No. 12/221,956 dated Feb. 16, 2011.
Ohkura et al., "Gastrin-Enhanced Tumor Growth of a Xenotransplantable Human Gastric Carcinoma in Nude Mice," Jpn. J. Clin. Oncol. vol. 10, No. 2 pp. 255-263 (1980).
Ohning et al., "Differential Kinetics for Immunoneutralization of Circulating Gastrin by Gastrin Monoclonal Antibody and its $Fab_1$ Fragment in Rats," Peptides. vol. 15 pp. 417-423 (1994).
Ohning et al., "Gastrin mediates the gastric mucosal proliferative response to feeding," American Journal of Physiology. vol. 271 (Gastrointest. Liver Physiol. 34) pp. G470-G476 (1996).
Ohsawa et al., "Effects of Three $H_2$-Receptor Antagonists (Cimetidine, Famotidine, Ranitidine) on Serum Gastrin Level," International Journal of Clinical Pharmacology Research. vol. 22, No. 2 pp. 29-35 (2002).
Ohtsu et al., "Randomized Phase III Trial of Fluorouracil Alone Versus Fluorouracil Plus Cisplatin Versus Uracil and Tegafur Plus Mitomycin in Patients With Unresectable, Advanced Gastric Cancer: The Japan Clinical Oncology Group Study (JCOG9205)," Journal of Clinical Investigation. vol. 21, No. 1 pp. 54-59 (2003).
Okada et al., "Evaluation of cholecystokinin, gastrin, CCK-A receptor, and CCK-B/gastrin receptor gene expressions in gastrin cancer," Cancer Letters. vol. 106, No. 2 pp. 257-262 (1996).

Onorato et al., "Immunohistochemical and ELISA Assays for Biomarkers of Oxidative Stress in Aging and Disease," Annals of New York Academy of Sciences. vol. 854 pp. 277-290 (1998).

Osband, M.E., and Ross, S., "Problems in the investigational study and clinical use of cancer immunotherapy," Immunology Today. vol. 1, No. 6 pp. 193-195 (1990).

Osin, P.P., and Lakhani, S.R., "The pathology of familial breast cancer: Immunohistochemistry and molecular analysis," Breast Cancer Research. vol. 1, No. 1 pp. 36-40 (1999).

Palnæs Hansen et al., "Metabolism and Influence of Glycine-Extended Gastrin on Gastric Acid Secretion in Man," Digestion. vol. 57 pp. 22-29 (1996).

Pannequin et al., "Divergent roles for ferric ions in the biological activity of amidated and non-amidated gastrins," Journal of Endocrinology. vol. 181, No. 2 pp. 315-325 (2004).

Parsonnet et al., "*Helicobacter pylori* Infection and the Risk of Gastric Carcinoma," The New England Journal of Medicine. vol. 325, No. 16 pp. 1127-1131 (1991).

Pauwels et al., "Identification of Progastrin in Gastrinomas, Antrum, and Duodenum by a Novel Radioimmunoassay," The Journal of Clinical Investigation. vol. 77 pp. 376-381 (1986).

Pawlikowski et al., "Gastrin and Somatostatin Levels in Patients with Gastric Cancer," Horm. Metabol. Res. vol. 21 pp. 89-91 (1989).

Petrelli et al., "The Modulation of Fluorouracil With Leucovorin in Metastatic Colorectal Carcinoma: A Prospective Randomized Phase III Trial," Journal of Clinical Oncology. vol. 7 pp. 1419-1426 (1989).

Petrioli et al., "Treatment of Advanced Colorectal Cancer with High-dose Intensity Folinic Acid and 5-Fluorouracil Plus Supportive Care," European Journal of Cancer. vol. 31A, No. 12 pp. 2105-2108 (1995).

Plested et al. "ELISA," Methods in Molecular Medicine. vol. 71 pp. 243-261 (2003).

Podlecki et al., "Nuclear Translocation of the Insulin Receptor: A Possible Mediator of Insulin's Long Term Effects," The Journal of Biological Chemistry. vol. 262, No. 7 pp. 3362-3368 (1987).

Power et al., "A novel gastrin-processing pathway in mammalian antrum," Chemical Abstracts. vol. 109, No. 9 p. 113 (1988) [Abstract # 109:67341z].

Rae-Venter et al., "Gastrin Receptors in Human Colon Carcinoma," Gastroenterology. vol. 80, No. 5, Part 2 p. 1256 (1981) [Abstract].

Rahier et al., "Biosynthesis of Gastrin: Localization of the Precursor and Peptide Products Using Electron Microscopic-Immunogold Methods," Gastroenterology. vol. 92 pp. 1146-1152 (1987).

Reddy, "Small Cell Lung Cancer: Improving Outcomes," American Society for Therapeutic Radiology and Oncology, 42nd Annual Meeting, Day 1, Oct. 22, 2000, meeting report published by Medscape.

Redmond, E.J., and Wetscher, G.J., "Gastroesophageal Reflux Disease," Ronald Hinder ed., R.G. Landes Company. pp. 1-6 (1993).

Rehfeld, "Gastrin and Colorectal Cancer: A Never-Ending Dispute?" Gastroenterology. vol. 108, No. 4 pp. 1307-1310 (1995).

Rehfeld, "The New Biology of Gastrointestinal Hormones," Physiological Reviews. vol. 78, No. 4 pp. 1087-1108 (1998).

Rehfeld, "Three Components of Gastrin in Human Serum," Biochimica et Biophysica Acta. vol. 285 pp. 364-372 (1972).

Rehfeld, J.F., and Johnsen, A.H., "Residue-specific immunochemical sequence prediction," Journal of Immunological Methods. vol. 171 pp. 139-142 (1994).

Rehfeld et al., "Cell-specific processing of pro-cholecystokinin and pro-gastrin," Biochimie. vol. 70 pp. 25-31 (1988).

Rehfeld et al., "Gastrin in Human Bronchogenic Carcinomas: Constant Expression but Variable Processing of Progastrin," Cancer Research. vol. 49 pp. 2840-2843 (1989).

Rehfeld et al., "Production and Evaluation of Antibodies for the Radioimmunoassay of Gastrin," Scnad. J. Clin. Lab. Invest. vol. 30 pp. 221-232 (1972).

Rehfeld et al., "Sulfation of Gastrin: Effect on Immunoreactivity," Regulatory Peptides. vol. 2 pp. 333-342 (1981).

Ritter et al., "Serological Analysis of Human Anti-Human Antibody Responses in Colon Cancer Patients Treated with Repeated Doses of Humanized Monoclonal Antibody A33," Cancer Research. vol. 61 pp. 6851-6859 (2001).

Robertson et al., "Effect of Gastrointestinal Hormones and Synthetic Analogues on the Growth of Pancreatic Cancer," Int. J. Cancer. vol. 63 pp. 69-75 (1995).

Rodriguez-Lescure et al., "Phase II Study of Gemcitabine (GEM) and Weekly 48-Hour Continuous Infusion (CI) with High Dose 5-Fluorouracil (5-FU) in Advanced Exocrine Pancreatic Cancer (APC)," Proceedings of the Annual Meeting of the American Society of Clinical Oncology. vol. 18, p. 298 (1999) [Abstract # 1145].

Romani et al. "Gastrin Receptor Antagonist CI-988 Inhibits Growth of Human Colon Cancer In Vivo and In Vitro," Aust. N.Z. J. Surgery. vol. 66 pp. 235-237 (1996).

Romani et al., "Potent new family of gastrin receptor antagonists (GRAs) produces in vitro and in vivo inhibition of human colorectal cancer (CRC) cell lines," Proceedings of the American Association for Cancer Research. vol. 35 p. 397 (1994) [Abstract # 2369].

Rondeel, "Immunofluorescence *versus* ELISA for the detection of antinuclear antigens," Expert Rev. Mol. Diagn. vol. 2, No. 3 pp. 226-232 (2002).

Rothenberg et al., "A phase II trial of gemcitabine in patients with 5-FU-refractory pancreas cancer," Annals of Oncology. vol. 7 pp. 347-353 (1996).

Scemama et al., "Characterisation of gastrin receptors on a rat pancreatic acinar cell line (AR42J). A possible model for studying gastrin mediated cell growth and proliferation," Gut. vol. 28, No. S1 pp. 233-236 (1987).

Scheele et al., "Indicators of prognosis after hepatic resection for colorectal secondaries," Surgery. vol. 110, No. 1 pp. 13-29 (1991).

Scheithauer et al., "Combined Intraperitoneal plus Intravenous Chemotherapy after Curative Resection for Colonic Adenocarcinome," European Journal of Cancer. vol. 31A, No. 12 pp. 1981-1986 (1995).

Schlom, "Monoclonal Antibodies: They're More and Less Than You Think," Molecular Foundations of Oncology. ed. Broder Williams & Williams, Baltimore MD, pp. 95-134 (1991).

Schmitz et al., "CCK-B/gastrin receptors in human colorectal cancer," European Journal of Clinical Investigation. vol. 31 pp. 812-820 (2001).

Seitz et al., "Elevated Serum Gastrin Levels in Patients with Colorectal Neoplasia," J. Clin. Gastroenterol. vol. 13, No. 5 pp. 541-545 (1991).

Senior, "Immunization blocks gastrin's ability to promote tumour cell division," Drug Discovery Today. vol. 6, No. 2 pp. 62-63 (2001).

Seva et al., "Characterization of the Glycine-Extended Gastrin (G-GLY) Receptor on AR4-2J Cells," Gastroenterology. vol. 108 p. A1005 (1995) [Abstract].

Seva et al., "Growth-Promoting Effects of Glycine-Extended Progastrin", Science. vol. 265, No. 5170 pp. 410-412 (1994).

Seva et al., "Lorglumide and Loxglumide Inhibit Gastrin-stimulated DNA Synthesis in a Rat Tumoral Acinar Pancreatic Cell Line (AR42J)," Cancer Research. vol. 50, No. 8 pp. 5829-5833 (1990).

Shewach, D.S., and Lawrence, T.S., "Radiosensitization of Human Solid Tumor Cell Lines With Gemcitabine," Seminars in Oncology. vol. 23, No. 5, Suppl. 10 pp. 65-71 (1996).

Shewach, D.S., "Metabolism of 2',2'-Difluoro-2'-Deoxycytidine and Radiation Sensitization of Human Colon Carcinoma Cells," Cancer Research. vol. 54 pp. 3218-3223 (1994).

Siemann, "Satisfactory and Unsatisfactory Tumor Models: Factors Influencing the Selection of a Tumor Model for Experimental Evaluation," Rodent Tumor Models in Experimental Cancer Therapy (Ed. Kallman) Pergamon Press, NY. pp. 12-15 (1987).

Singh et al., "Gut hormones in colon cancer: past and prospective studies," Cancer Journal. vol. 3, No. 1 pp. 28-33 (1990).

Singh et al., "High Levels of Progastrin Significantly Increase Premalignant Changes in Colonic Mucosa of Mice in Tesponse to the Chemical Carcinogen, AOM," Gastroenterology. vol. 114, No. 4 p. A680 (1998) [Abstract # G2810].

Singh et al., "Incomplete processing of progastrin expressed by human colon cancer cells: roles of noncarboxyamidated gastrins," The American Physiological Society. pp. G459-G468 (1994).

Singh et al., "Novel Gastrin Receptors Mediate Mitogenic Effects of Gastrin and Processing Intermediates of Gastrin on Swiss 3T3 Fibroblasts. Absence of Detectable Cholecystokinin (CCK)-A and CCK-B Receptors," The Journal of Biological Chemistry. vol. 270, No. 15 pp. 8429-8438 (1995).

Singh et al., "Role of Gastrin and Gastrin Receptors on the Growth of a Transplantable Mouse Colon Carcinoma (MC-26) in BALB/c Mice," Cancer Research. vol. 46 pp. 1612-1616 (1986).

Sipponen et al., "Serum Levels of Amidated Gastrin-17 and Pepsinogen I in Atrophic Gastritis: An Observational Case-Control Study," Scandinavian Journal of Gastroenterology. vol. 37, No. 7 pp. 785-791 (2002).

Slooter et al., "Tumor growth stimulation after partial hepatectomy can be reduced by treatment with tumor necrosis factor α," British Journal of Surgery. vol. 82 pp. 129-132 (1995).

Smith, A.M., and Watson, S.A., "Gastrin and gastrin receptor activation: an early event in the adenoma-carcinoma sequence," Gut. vol. 47, No. 6 pp. 820-824 (2000).

Smith, A.M., and Watson, S.A., "Review Article: Gastrin and Colorectal Cancer," Alimentary Pharmacology & Therapeutics. vol. 14, No. 10 pp. 1231-1247 (2000).

Smith, J.P., and Solomon, T.E., "Effects of Gastrin, Proglumide, and Somatostatin on Growth of Human Colon Cancer," Gastroenterology. vol. 95, No. 6 pp. 1541-1548 (1988).

Smith et al., "Antisense oligonucleotides to gastrin inhibit growth of human pancreatic cancer," Cancer Letters. vol. 135 pp. 107-112 (1999).

Smith et al., "Characterization of the CCK-C (cancer) receptor in human pancreatic cancer," International Journal of Molecular Medicine. vol. 10, No. 6 pp. 689-694 (2002).

Smith et al., "Elevated Gastrin Levels in Patients with Colon Cancer or Adenomatous Polyps," Digestive Diseases and Science. vol. 34, No. 2 pp. 171-174 (1989).

Smith et al., "Gastric carcinoid expresses the gastrin autocrine pathway," British Journal of Surgery. vol. 85 pp. 1285-1289 (1998).

Smith et al., "Gastrin may have an autocrine/paracrine role in Barrett's oesophagus and oesophageal adenocarcinoma," British Journal of Surgery. vol. 84 pp. 706-707 (1996).

Smith et al. "Gastrin regulates growth of human pancreatic cancer in a tonic and autocrine fashion," American Journal of Physiology. vol. 270, No. 39 (Regulatory Integrative Comp. Physiol. 39) pp. R1078-R1084 (1996).

Smith et al., "Identification and characterization of CCK-B/gastrin receptors in human pancreatic cancer cell lines," American Journal of Physiology. vol. 266 pp. R277-R283 (1994).

Smith et al. "Identification of gastrin as a growth peptide in human pancreatic cancer," American Journal of Physiology. vol. 268 (Regulatory Integrative Comp. Physiol. 37) pp. R135-R141 (1995).

Smith et al., "Phase I/II Study of G17-DT, an Anti-Gastrin Immunogen, in Advanced Colorectal Cancer," Clinical Cancer Research. vol. 6, No. 12 pp. 4719-4724 (2000).

Smith et al., "Sensitivity of the Esophageal Mucosa to pH in Gastroesophageal Reflux Disease," Gastroenterology. vol. 96 pp. 683-689 (1989).

Sobhani et al., "Chronic Endogenous Hypergastrinemia in Humans: Evidence for a Mitogenic Effect on the Colonic Mucosa," Gastroenterology. vol. 105, No. 1 pp. 22-30 (1993).

Sobhani et al., "Immunohistochemical characterization of gastrinomas with antibodies specific to different fragments of progastrin," Gastroentérologie Clinique et Biologique. vol. 13, No. 11 pp. 865-872 (1989).

Soll et al. "Gastrin-Receptors on Isolated Canine Parietal Cells," The Journal of Clinical Investigation, Inc.. vol. 73 pp. 1434-1447 (1984).

Song et al., "The human gastrin/cholecystokinin type B receptor-gene: Alternative splice donor site in exon 4 generates two variant mRNAs," PNAS. vol. 90, No. 19 pp. 9085-9089 (1993).

Spitler, L.E. "Cancer Vaccines: The Interferon Analogy," Cancer Biotherapy. vol. 10, No. 1 pp. 1-3 (1995).

Stepan et al., "Glycine-Extended Gastrin Exerts Growth-Promoting Effects on Colon Cancer Cell Lines," Gastroenterology. vol. 110, No. 4 p. A1122 (1996) [Abstract].

Stepan et al., "Glycine-Extended Gastrin Exerts Growth-Promoting Effects on Human Colon Cancer Cells," Molecular Medicine. vol. 5, No. 3 pp. 147-159 (1999).

Stubbs et al., "Correlation between Uptake of Labeled Anti-CCKB/Gastrin Receptor Antibodies and the Occurrence of Apoptosis in Hepatoma Cell Lines," Gastroenterology. vol. 122, No. 4, Suppl. 1 p. A-380 (2002) [Abstract # T915].

Stubbs et al., "Endocytosis of Anti-CCK-B/Gastrin Receptor Antibody and Effect on Hepatoma Cell Lines," The Journal of Histochemistry & Cytochemistry. vol. 50, No. 9 pp. 1213-1217 (2002).

Sugano, et al., "Identification and Characterization of Glycine-extended Post-translational Processing Intermediates of Progastrin in Porcine Stomach," The Journal of Biological Chemistry. vol. 260, No. 21 pp. 11724-11729 (1985).

Sundler et al., "The Neuroendocrine System of the Gut—An Update," Acta Oncologica. vol. 30, No. 4 pp. 419-427 (1991).

Takhar et al., "The role of gastrin in colorectal carcinogenesis," J.R. Coll. Surg. Edinb. Irel. vol. 2, No. 5 pp. 251-257 (2004).

Takinami et al., "YF476 is a new potent and selective gastrin/cholecystokinin-B receptor antagonist in vitro and in vivo," Ailment Pharmacol. Ther. vol. 11, No. 1 pp. 113-120 (1997).

Talley et al., "Risk for Colorectal Adenocarcinoma in Pernicious Anemia," Annals of Internal Medicine. vol. 111, No. 9 pp. 738-742 (1989).

Tang et al., "Expression of receptors for gut peptides in human pancreatic adenocarcinoma and tumor-free pancreas," British Journal of Cancer. vol. 75, No. 10 pp. 1467-1473 (1997).

Taniguchi et al., "Cholecystokinin-B/gastrin receptor signaling pathway involves tyrosine phosphorylations of p125FAK and p42MAP," Oncogene. vol. 9 pp. 861-867 (1994).

Tarasova et al., "Anti-peptide antibodies specific for the gastrin/cholecystokinin-B receptor," Letters in Peptide Science. vol. 1 pp. 221-228 (1994).

Tarasova et al., "Endocytosis of gastrin in cancer cells expressing gastrin/CCK-B receptor," Cell and Tissue Research. vol. 287 pp. 325-330 (1997).

Taylor, "Chemotherapy, radiotherapy and immunotherapy of colorectal neoplasia," Current Opinion in Gastroenterology. vol. 9 pp. 28-33 (1993).

Tetin, S.Y., and Stroupe, S.D., "Antibodies in Diagnostic Applications," Current Pharmaceutical Biotechnology. vol. 5, No. 1 pp. 9-16 (2004).

Thorndyke, M., and Dockray, G.J., "Identification and localization of material with gastrin-like immunoreactivity in the neutral ganglion of a photochordate, *Ciona intestinalis*," Regulatory Peptides. vol. 16 pp. 269-279 (1986).

Tielemans et al., "Proliferation of Enterochromaffinlike Cells in Omeprazole-Treated Hypergastrinemic Rats," Gastroenterology. vol. 96, No. 3 pp. 723-729 (1989).

Todisco et al., "Gastrin and Glycine-extended Progastrin Processing Intermediates Induce Different Programs of Early Gene Activation," The Journal of Biological Chemistry. vol. 270, No. 47 pp. 28337-28341 (1995).

Torosian et al., "Colon Carcinoma Metastatic to the Thigh—An Unusual Site of Metastasis. Report of a Case," Diseases of the Colon and Rectum. vol. 30, No. 10 pp. 805-808 (1987).

Trakal et al., "Diagnosis and Etiology of Barrett's Esophagus: Presence of Gastrin Secreting Cells," Acta Gastroenterològica Latinoamericana. vol. 15, No. 2 pp. 67-80 (1985) [Abstract].

Tschmelitsch et al., "Enhanced Antitumor Activity of Combination Radioimmunotherapy ($^{131}$I-labeled Monoclonal Antibody A33) with Chemotherapy (Fluorouracil)," Cancer Research. vol. 57 pp. 2181-2186 (1997).

Ullrich et al. "Signal Transduction by Receptors with Tyrosine Kinase Activity," Cell. vol. 61 pp. 203-212 (1990).

UniProtKB/Swiss-Prot entry P01350, (1986) (accessed on Mar. 26, 2007).

Upp et al., "Clinical Significance of Gastrin Receptors in Human Colon Cancers" Cancer Research. vol. 49 pp. 488-492 (1989).

Upp et al., "Polyamine Levels and Gastrin Receptors in Colon Cancers" Ann. Surg. vol. 207, No. 6 pp. 662-668 (1988).

Väänänen et al. "Non-endoscopic diagnosis of atrophic gastritis with a blood test. Correlation between gastric histology and serum levels of gastrin-17 and pepsinogen I: a multicentre study," European Journal of Gastroenterology & Hepatology. vol. 15, No. 8 pp. 885-891 (2003).

Vaillant et al., "Cellular Origins of Different Forms of Gastrin. The Specific Immunocytochemical Localization of Related Peptides," The Journal of Histochemistry and Cytochemistry. vol. 27, No. 5 pp. 932-935 (1979).

Vaillant et al., "Repeat liver resection for recurrent colorectal metastasis," British J. Surgery. vol. 80, No. 3 pp. 340-344 (1993).

Van Cutsem et al., "Phase III Study of Docetaxel Cisplatin Plus Fluorouracil Compared With Cisplatin and Fluorouracil as First-Line Therapy for Advanced Gastric Cancer: A Report of the V325 Study Group," Journal of Clinical Oncology. vol. 24, No. 31 pp. 4991-4997 (2006).

Van Solinge et al., "Expression but Incomplete Maturation of Progastrin in Colorectal Carcinomas," Gastroenterology. vol. 104 pp. 1099-1107 (1993).

Vanhoefer et al., "Final Results of a Randomized Phase III Trial of Sequential High-Dose Methotrexate, Fluorouracil, and Doxorubicin Versus Etoposide, Leucovorin, and Fluorouracil Versus Infusional Fluorouracil and Cisplatin in Advanced Gastric Cancer: A Trial of the European Organization for Research and Treatment of Cancer Gastrointestinal Tract Cancer Cooperative Group," Journal of Clinical Oncology. vol. 18, No. 14 pp. 2648-2657 (2000).

Varndell et al., "Intracellular topography of immunoreactive gastrin demonstrated using electron immunocytochemistry," Experienta. vol. 39 pp. 713-717 (1983).

Varro, A., and Ardill, J.E.S., "Gastrin: an analytical review," Ann. Clin. Biochem. vol. 40 pp. 472-480 (2003).

Varro, A., and Dockray, G.J., "Post-translational processing of progastin: inhibition of cleavage, phosphorylation and sulphation by brefeldin A," Biochem. J. vol. 295 pp. 813-819 (1993).

Varro et al., "Discrimination between Temperature- and Brefeldin A-sensitive Steps in the Sulfaction, Phosphorylation, and Cleavage of Progastrin and Its Derivatives," The Journal of Biological Chemistry. vol. 269, No. 32 pp. 20764-20770 (1994).

Varro et al., "Pathways of Processing of the Gastrin Precursor in Rat Antral Mucosa," Journal of Clinical Investigation. vol. 95 pp. 1642-1649 (1995).

Varro et al., "The human gastrin precursor," Biochem. J. vol. 256 pp. 951-957 (1988).

Vauthey et al., "Factors Affecting Long-Term Outcome After Hepatic Resection for Hepatocellular Carcinoma," The American Journal of Surgery. vol. 169 pp. 28-35 (1995).

Von Hoff, D.D., and Bearss, D., "New drugs for patients with pancreatic cancer," Curr. Opin. Oncology. vol. 14 pp. 621-627 (2002).

Wang et al., "Processing and Proliferative Effects of Human Progastrin in Transgenic Mice," Journal of Clinical Investigation. vol. 98, No. 8 pp. 1918-1929 (1996).

Wank, "Cholecystokinin receptors," Am. J. Physiol. vol. 269 (Gastrointest. Liver Physiol.) pp. G628-G646 (1995).

Wank et al., "Brain and gastrointestinal cholecystokinin receptor family: Structure and functional expression," PNAS. vol. 89 pp. 8691-8695 (1992).

Wank et al., "Cholecystokinin Receptor Family. Molecular Cloning, Structure, and Functional Expression in Rat, Guinea Pig, and Human," Annals New York Academy of Sciences. vol. 713 pp. 49-66 (1994).

Watson, "Gastrin antagonists and gastrointestinal tumours," Expert Opinion on Investigational Drugs. vol. 4, No. 12 pp. 1253-1266 (1995).

Watson, S.A. and Gilliam, A.D., "G17DT—a new weapon in the therapeutic armoury for gastrointestinal malignancy," Expert Opinion on Biological Theory. vol. 1, No. 2 pp. 309-317 (2001).

Watson, S.A., and Smith, A.M., "Hypergastrinemia Promotes Adenoma Progression in the APCMin–/+ Mouse Model of Familial Adenomatous Polyposis," Cancer Research. vol. 61 pp. 625-631 (2001).

Watson, S., and Steele, R., "Gastrin Receptors in Gastrointestinal Tumors," CRC Press. Boca Raton, Florida. pp. 1-36, 43-61 and 63-99 (1993).

Watson, S.A., and Steele, R.J.C., "Gastrin antagonists in the treatment of gastric cancer," Anti-Cancer Drugs. vol. 4, No. 6 pp. 599-604 (1993).

Watson et al., "A Comparison of an Anti-Gastrin Antibody and Cytotoxic Drugs in the Therapy of Human Gastric Ascites in SCID Mice," International Journal of Cancer. vol. 81 No. 2 pp. 248-254 (1999).

Watson et al., "Anti-Gastrin Antibody Raised by Gastrimmune Inhibit Growth of the Human Colorectal Tumour AP5," International Journal of Cancer. vol. 61, No. 2 pp. 233-240 (1995).

Watson et al., "Antibodies Raised by Gastrimmune Inhibit the Spontaneous Metastasis of a Human Colorectal Tumour, AP5LV," European Journal of Cancer. vol. 35, No. 8 pp. 1286-1291 (1999).

Watson et al., "Antibodies Targeting the Amino Terminal Portion of the Human CCKB/Gastrin Receptor Inhibit the Liver Invasion of a Human Colonic Tumour," Gastroenterology. vol. 114, No. 4, Part 2 p. A701 (1998) [Abstract # G2899].

Watson et al., "Antibodies targeting the Amino Terminal portion of the Human CCKB/gastrin receptor inhibit the liver invasion of a human colonic tumour," Research Presentation, Digestive Disease Week, American Gastroenterological Association (1998), 17 slides.

Watson et al., "Antiserum Raised against an Epitope of the Cholecystokinin B/Gastrin Receptor Inhibits Hepatic Invasion of a Human Colon Tumor," Cancer Research. vol. 60, No. 20 pp. 5902-5907 (2000).

Watson et al., "Detection of Gastrin Receptors on Gastrointestinal Tumours Using the Anti-Gastrin Receptor Monoclonal Antibody, 2CL," Gut. vol. 4 p. S68 (1993) [Abstract # F271].

Watson et al., "Effect of Gastrin Neutralization on the Progression of the Adenoma:Carcinoma Sequence in the *Min* Mouse Model of Familial Adenomatous Polyposis," Gastroenterology. vol. 114, No. 4, Pt. 2 p. A701 (1998) [Abstract # G2900].

Watson et al., "Enhanced Inhibition of Pancreatic Cancer by Combination of the G17DT Immunogen and Gemcitabine," Amer. Soc. Clin. Oncol. vol. 37 (2002) [Abstract] (2 pages).

Watson et al., "Expression of CCKB/Gastrin Receptor Isoforms in Gastro-Intestinal Tumour Cells," International Journal of Cancer. vol. 77, No. 4 pp. 572-577 (1998).

Watson et al., "Expression of gastrin/CCKB receptor isoforms in gastrointestinal tumor cells: Relationship to gastrin secretion," Proceedings of the American Association for Cancer Research Annual Meeting. vol. 38 p. 116 (1997) [Abstract # 773].

Watson et al., "Gastrin: growth enhancing effects on human gastric and colonic tumour cells," British Journal of Cancer. vol. 59, No. 4 pp. 554-558 (1989).

Watson et al., "Gastrin Inhibition Increases the Potency of Cytotoxic Agents in Pancreatic Cancer," Gastroenterology. vol. 122, No. 4 p. A-241 (2002) [Abstract # M952].

Watson et al., "Growth-promoting action of gastrin on human colonic and gastric tumour cells cultured in vitro," British Journal of Surgery. vol. 75, No. 4 pp. 342-345 (1998).

Watson et al., "Inhibition of Gastrin-stimulated Growth of Gastrointestinal tumour cells by Octreotide and the Gastrin/Cholecystokinin Receptor Antagonists, Proglumide and Lorglumide," European Journal of Cancer. vol. 28A, No. 8/9 pp. 1462-1467 (1992).

Watson et al., "Inhibitory Effects of the Gastrin Receptor Antagonist (L-365,260) on Gastrointestinal Tumor Cells," Cancer. vol. 68 pp. 1255-1260.

Watson et al., "Intracellular Gastrin in Human Gastrointestinal Tumor Cells," Journal of National Cancer Institute. vol. 83, No. 12 pp. 866-871 (1991).

Watson et al., "Synergistic inhibitory effects of G17DT on gastrointestinal tumour growth in combination with cytotoxic agents," Proc. Am. Soc. Clin. Oncol. vol. 22 (2003) [Abstract # 3497] (3 pages).

Watson et al., "The Effect of the $E_2$ Prostaglandin Enprostil, and the Somatostatin Analogue SMS 201 995, on the Growth of a Human Gastric Cell Line, MKN45G," International Journal of Cancer. vol. 45 pp. 90-94. (1990).

Watson et al., "The In Vitro Growth Response of Primary Human Colorectal and Gastric Cancer Cells to Gastrin," International Journal of Cancer. vol. 43 pp. 692-696 (1989).

Watson et al., "Therapeutic effect of the gastrin receptor antagonist, CR2093 on gastrointestinal tumour cell growth," British Journal of Cancer. vol. 65, No. 6 pp. 879-883 (1992).

Weinberg et al., "Cholecystokinin A and B Receptors Are Differentially Expressed in Normal Pancreas and Pancreatic Adenocarcinoma," The Journal of Clinical Investigation. vol. 100, No. 3 pp. 597-603 (1997).

Weiner, L.M., "An Overview of Monoclonal Antibody Therapy of Cancer," Seminars in Oncology. vol. 26, No. 4, Suppl. 12 pp. 41-50 (1999).

Weinstock et al., "Binding of Gastrin$_{17}$ to Human Gastric Carcinoma Cell Lines," Cancer Research. vol. 48, No. 4 pp. 932-937 (1988).

Wendlberger et al, "The syntheses of human big gastrin I and its 32-leucine analog" Chemical Abstracts. vol. 92, No. 21 p. 722 (1980) [Abstract # 92:198749s].

Wetscher et al., "Pathophysiology of Gastroesophageal Reflux Disease," R.A. Heinder ed., R.G. Landes Co., Chapter 2 pp. 7-29 (1993).

Wong et al., "Postprandial hypergastrinaemia in patients with colorectal cancer," Gut. vol. 32 pp. 1352-1354 (1991).

Written Opinion corresponding to International Patent Application No. PCT/US2004/009666 dated Nov. 7, 2004.

Wunsch, E., and Moroder, L., "Biological and Immunological Properties of Human Gastrin I Analogues," Hoppe-Syeler's Z. Physiol. Chem. vol. 363 pp. 665-669 (1982).

Yamaguchi et al., "Amino-terminal immunoreactivity of big gastrin in plasma and tumors obtained from patients with Zollinger-Ellison Syndrome," Chem. Abstracts. vol. 100 p. 373 (1984) [Abstract # 100:154661m].

Yanaihara et al. "A New Type of Gastrin Derivative and its Use for Production of Central Region-Specific Anti-Gastrin Sera," Biomedical Research. vol. 1 pp. 242-247 (1980).

Yanaihara et al. "Human Big Gastrin N-Terminal Fragment Immunoreactivity," Gut Peptides, Elsevier, North-Holland Biomed. Press, pp. 26-33 (1979).

Yardley, "Gemcitabine and docetaxel in metastatic and neoadjuvant treatment of breast cancer," Semin. Oncol. vol. 31, No. 2, Suppl. 5 pp. 37-44 (2004).

Yuki et al., "YM022, A Potent and Selective Gastrin/CCK-B Receptor Antagonist, Inhibits Peptone Meal-Induced Gastric Acid Secretion in Heidenhain Pouch Dogs," Digestive Diseases and Sciences. vol. 42, No. 4 pp. 707-714 (1997).

Zeitoun, "Comparison of Omeprazole with Ranitidine in the Treatment of Reflux Oesophagitis," Scand. J. Gastroenterol. vol. 24, Suppl. 166 pp. 83-87 (1989).

Zeng et al., "Localization of PACAP Receptors on Rat Fundic ECL and D Cells,"Gastroenterology. vol. 110, Suppl. 4 p. A1136 (1996) [Abstract].

Zhou et al., "Pre- and Postoperative Sequential Study on the Serum Gastrin Level in Patients with Lung Cancer," Journal of Surgical Oncology. vol. 51 pp. 22-25 (1992).

"Clinical Trial Initiated with Chemorefractory Patients," Cancer Weekly, The Gale Group, (Jan. 9, 2001).

"Clinical trials update," Scrip, Informa UK Ltd., No. 2547 p. 25 (Jun. 9, 2000).

"Development and Activity of 5-FU," CancerQuest, http://www.cancerquest.org/index.cfm?page=443 (accessed on Aug. 13, 2004) 1 pg.

"Other News to Note," Bioworld Today, American Health Consultants Inc., vol. 11, No. 82 pp. 1-8 (Apr. 27, 2000).

"ADAP drugs: leucovorin," Access Project, http://www.aegis.com/factshts/network/access/drugs/leuc.html (1996) (accessed on Aug. 13, 2004), 1 page.

"*Prilosec* OTC Review: Two Advisory Committee Members Weigh in Without Voting," The Pink Sheet. pp. 22-23 (2002).

Abdalla et al., "Gastrin-Induced Cyclooxygenase-2 Expression in Barrett's Carcinogenesis," Clinical Cancer Research. vol. 10 pp. 4784-4792 (2004).

Abrahm et al., "Development and Evaluation of a High Affinity Species and Region Specific Monoclonal Antibody to Human Gastrin," Gastroenterology. vol. 86, No. 5, Part 2 p. 1012 (1984).

Ajani et al., "Phase I and II Studies of the Combination of Recombinant Human Interferon-γ and 5-Fluorouracil in Patients with Advanced Colorectal Carcinoma," Journal of Biological Response Modifiers. vol. 8, No. 2 pp. 140-146 (1989).

Akai, "Co-Existence and Co-Release of Gatrin 34 N-Terminal Fragment With Gastrin 17 in Rat Stomach," Folla endocrinol. vol. 64 pp. 1065-1080 (1988) [Abstract].

Aphton Biopharma BIO2005 Presentation, Jun. 19-22, Philadelphia, PA (2005), 26 pages.

Ardill et al., "Autoantibodies to gastrin in patients with pernicious anaemia—a novel antibody," Q. J. Med. vol. 91 pp. 739-742 (1998).

Ardis R&D Profile, "Gastrin 17 vaccine—Aphton: Anti-gastrin 17 immunogen, G17DT," Biodrugs. vol. 17, No. 3 pp. 223-225 (2003).

Asao et al., "Eradication of Hepatic Metastases of Carcinome H-59 by Combination Chemimmunotherapy with Liposomal Muramyl Tripeptide, 5-Fluorouracil, and Leucovorin," Cancer Research. vol. 52 pp. 6254-6257 (1992).

Ausubel, ed., "Current Protocols in Molecular Biology," John Wiley & Sons, New York, pp. 11.15.1-11.15.9. (2002).

Azuma et al., "Immunocytochemical Evidence for Differential Distribution of Gastrin Forms Using Region-Specific Antibodies," Gastroenterologia Japonica. vol. 21, No. 4 pp. 319-324 (1986).

Baba et al., "Glycine-Extended Gastrin Induces Matrix Metalloproteinase-1- and 3-Mediated Invasion of Human Colon Cancer Cells Through Type 1 Collagen Gel and Matrigel," International Journal of Cancer. vol. 111, No. 1 pp. 23-31 (2004).

Bailey, "Radioimmunoassay of Peptides and Proteins," Methods in Molecular Biology. vol. 32 pp. 449-459 (1994).

Baldwin et al., "Binding of the progastrin fragments to the 78 kDa gastrin-binding protein," FEBS Lett. vol. 359 pp. 97-100 (1995).

Baldwin, G.S., and Zhang, Q., "Measurement of Gastrin and Transforming Growth Factor α Messenger RNA Levels in Colonic Carcinoma Cell Lines by Quantitative Polymerase Chain Reaction," Cancer Research. vol. 52 pp. 2261-2267(1992).

Baldwin, G.S. and Shulkes, A., "Gastrin, gastrin receptors and colorectal carcinoma," Gut. vol. 42 pp. 581-584 (1998).

Ballantyne, G.H., and Quin, J., "Surgical Treatment of Liver Mestastasis in Patients with Colorectal Cancer," Cancer. vol. 71, No. 12 pp. 4252-4266 (1993).

Beacham et al., "Human Gastrin: Isolation, Structure and Synthesis: Synthesis of Human Gastrin I," Nature. vol. 209, No. 5023 pp. 585-586 (1966).

Behr et al., "Cholecystokinin-B/Gastrin Receptor Binding Peptides: Preclinical Development and Evaluation of Their Diagnostic and Therapeutic Potential," Clinical Cancer Research. vol. 5 pp. 3124s-3138s (1999).

Beinborn et al., "A single amino acid of the cholecystokinin-B/gastrin receptor determines specificity for non-peptide antagonists," Nature. vol. 362 pp. 348-350 (1993).

Belani, C., "Paclitaxel and Docetaxel Combinations in Non-Small Cell Lung Cancer," Chest. vol. 117 pp. 144S-151S (2000).

Bentley et al., "Human Gastrin: Isolation, Structure and Synthesis," Nature. vol. 209, No. 5023 pp. 583-585 (1966).

Berg et al. In "Biochemistry," New York: W.H. Freeman and Co., 4.3.1-4.3.3 and Figure 4.35 (2002).

Biagini et al., "The Human Gastrin/Cholecystokinin Receptors: Type B and Type C Expression in Colonic Tumours and Cell Lines," Life Sciences. vol. 61, No. 10 pp. 1009-1018 (1997).

Blackmore et al. "Autocrine Growth Stimulation of Human Renal Wilms' Tumour G401 Cells by a Gastrin-Like Peptide," International Journal of Cancer. vol. 57 pp. 385-393 (1994).

Bock et al., "Benzodiazepine Gastrin and Brain Cholecystokinin Receptor Ligands: L-365,260," Journal of Medicinal Chemistry. vol. 32, No. 1 pp. 13-16 (1989).

Bodey, "The significance of immunohistochemistry in the diagnosis and therapy neoplasms," Expert Opin. Biol. Ther. vol. 2, No. 4 pp. 371-393 (2002).

Boland, "Editorial: Gastrin and Colorectal Neoplasia—Chicken or Egg, or Both?" J. Clin. Gastroenterology. vol. 13, No. 5 pp. 497-499 (1991).

Bold et al., "Gastrin Stimulates Growth of Human Colon Cancer Cells Via a Receptor Other Than CCK-A or CCK-B," Biochemical and Biophysical Research Communications. vol. 202, No. 3 pp. 1222-1226 (1994).

Boon, "Toward a Genetic Analysis of Tumor Rejection Antigens," Advances in Cancer Research. vol. 58 pp. 177-210 (1992).

Bowie et al., "Deciphering the Message in Protein Sequences: Tolerance to Amino Acid Substitutions," Science. vol. 247 pp. 1306-1310 (1990).
Brett et al., "Lymphocyte Expression of the CCK-B/Gastrin Receptor (CCK-BR) in Gastric Lymphomas, *Helicobacter pylori* Gastritis and Normal Gastric Biopsies," Gastroenterology. vol. 114, No. 4, Suppl. 1 p. A570 (1998) [Abstract # G2333].
Brett et al., "The Effect of Antibodies Raised Against Gastrimmune on the Proliferation of Human Pancreatic Carcinoma Cell Lines," Gut. vol. 42 p. A26 (1998) [Abstract # W190].
Brinton et al., "Cancer risk following pernicious anaemia," Br. J. Cancer. vol. 59, No. 5 pp. 810-813 (1989).
Bruns et al., "Therapy of Human Pancreatic Carcinoma Implants by Irinotecan and the Oral Immunomodulator JBT 3002 is Associated with Enhanced Expression of Inducible Nitric Oxide Synthase in Tumor-infiltrating Macrophages," Cancer Research. vol. 60 pp. 2-7, 2000.
Buchan et al., "Regulatory Peptides in Barrett's Esophagus," Journal of Pathology. vol. 146, No. 3 pp. 227-234 (1985).
Budavari et al., The Merck Index (11$^{th}$ ed.), Rahway, New Jersey, Merck & Co., p. 1082 (1989).
Burkitt et al., "Importance of gastrin in the pathogenesis and treatment of gastric tumors," World J. Gastroenterol. vol. 15, No. 1 pp. 1-16 (2009).
Burris III et al., "Improvements in survival and clinical benefit with gemcitabine as first-line therapy for patients with advanced pancreas cancer: a randomized trial," Journal of Clinical Oncology. vol. 15, No. 6 pp. 2403-2413 (1997).
Bystryn, J., "Tumor vaccines," Cancer and Metastasis Reviews. vol. 9 pp. 81-91 (1990).
Caplin et al., "Effect of Gastrin and Anti-Gastrin Antibodies on Proliferation of Hepatocyte Cell Lines," Digestive Diseases and Sciences. vol. 46, No. 7 pp. 1356-1366 (2001).
Caplin et al., "Expression and processing of gastrin in hepatocellular carcinoma, fibromellar carcinoma and cholangiocarcinoma," Journal of Hepatology. vol. 30, No. 3 pp. 519-526 (1999).
Caplin et al., "Expression and processing of gastrin in pancreatic adenocarcinoma," Brit. J. Surgery. vol. 87 pp. 1035-1040 (2000).
Caplin et al., "Expression and Processing of Gastrin in Patients with Pancreatic Carcinoma," Gastroenterology. vol. 114, Suppl. 1 p. A445 (1998) [Abstract # G1809].
Caplin et al., "Serum Gastrin Levels and Identification of CCK-B/gastrin Receptor Following Partial Hepatectomy for Liver Tumours in Man," Gastroenterology. vol. 110, Suppl. 4 p. A1162 (1996) [Abstract].
Caplin et al., "The CCK-B/Gastrin Receptor in Hepatocellular Carcinoma," Gastroenterology. vol. 110, No. 4 p. A1162 (1996) [Abstract].
Caplin et al., "Demonstration of new sites of expression of the CCK-B/gastrin receptor in pancreatic acinar AR42J cells using immunoelectron microscopy," Regulatory Peptides. vol. 84, Nos. 1-3 pp. 81-89 (1999).
Caplin et al., "Expression and Processing of Gastrin in Patients with Hepatocellular Carcinoma, Fibrolamellar Carcinoma and Cholangiocarcinoma," Gastroenterology. vol. 114, Suppl. I p. A1219 (1998) [Abstract # L0083].
Casper et al., "Phase II trial of gemcitabine (2,2'-difluorodeoxycitidine) in patients with adenocarcinoma of the pancreas," Investigational New Drugs. vol. 12, No. 1 pp. 29-34 (1994) [Abstract].
Certificate of Patent corresponding to Japanese Patent Application No. 2006-509465 dated Feb. 25, 2011.
Certified English Translation of PCT Patent Application No. WO2001/13114, "Use of stabilized synthetic compounds in immunoassay." Publication date: Feb. 22, 2001.
Chaudhry et al., "Phase I and Imaging Trial of a Monoclonal Antibody Directed Against Gastrin-releasing Peptide in Patients with Lung Cancer," Clinical Cancer Research. vol. 5 pp. 3385-3393 (1999).
Choudhury et al., "N-Terminal Sequence of Human Big Gastrin: Sequence, Synthetic and Immunochemical Studies," A76 Hoppe-Seyler's Z. Physiol. Chem. vol. 361 pp. 1719-1733 (1980).

Ciccotosto et al., "Expression, Processing, and Secretion of Gastrin in Patients With Colorectal Carcinoma," Gastroenterology. vol. 109, No. 4 pp. 1142-1153 (1995).
Clerc et al., "Differential Expression of the CCK-A and CCK-B/Gastrin Receptor Genes in Human Cancers of the Esophagus, Stomach, and Colon," International Journal of Cancer. vol. 72 pp. 931-936 (1997).
International Search Report corresponding to International Patent Application No. PCT/IB2005/002793 dated Dec. 7, 2005.
Interview Summary corresponding to U.S. Appl. No. 11/663,126 dated Nov. 15, 2011.
Nemeth et al., "A Gasztrin Aminoterminalis 1-13 Fragmensével Kidolgozott,Szekvenciaspecifikus Radioimmunoassay," Izotoptechnika. vol. 25, No. 4 pp. 288-294 (1982) [Abstract].
Non Opposition Notice corresponding to European Patent Application No. 97905858.3-2401 dated Feb. 17, 2012.
Notice of Acceptance corresponding to Australian Patent Application No. 2005286164 dated May 15, 2012.
Notice of Allowance corresponding to Canadian Patent Application No. 2,520,010 dated Nov. 22, 2011.
Notice of Allowance corresponding to U.S. Appl. No. 11/663,126 dated Jan. 6, 2012.
Nowak et al., "Gemcitabine Exerts a Selective Effect on the Humoral Immune Response: Implications for Combination Chemo-immunotherapy," Cancer Research. vol. 62 pp. 2353-2358 (2002).
Nowak et al., "Synergy between Chemotherapy and Immunotherapy in the Treatment of Established Murine Solid Tumors," Cancer Research. vol. 63 pp. 4490-4496 (2003).
Official Action corresponding to Australian Patent Application No. 2005286164 dated Oct. 4, 2011.
Official Action corresponding to Canadian Patent Application No. 2,580,965 dated Feb. 27, 2012.
Official Action corresponding to Chinese Patent Application No. 200580017341.9 dated Dec. 7, 2011.
Official Action corresponding to Indonesian Patent Application No. WO 00 2007 00931 dated Oct. 5, 2011.
Official Action corresponding to Israeli Patent Application No. 182012 dated Jul. 12, 2011.
Official Action corresponding to Japanese Patent Application No. 2006-310647 dated May 29, 2012.
Official Action corresponding to Japanese Patent Application No. 2007-506474 dated Jun. 7, 2011.
Official Action corresponding to Japanese Patent Application No. 2011-034753 dated May 29, 2012.
Official Action corresponding to Japanese Patent Application No. Hei10-549578 dated May 9, 2006.
Official Action corresponding to U.S. Appl. No. 09/700,329 dated Dec. 17, 2001.
Official Action corresponding to U.S. Appl. No. 09/700,329 dated Apr. 3, 2003.
Official Action corresponding to U.S. Appl. No. 09/700,402 dated Mar. 27, 2007.
Official Action corresponding to U.S. Appl. No. 09/700,402 dated Oct. 25, 2007.
Official Action corresponding to U.S. Appl. No. 10/235,236 dated Aug. 10, 2005.
Official Action corresponding to U.S. Appl. No. 10/323,692 dated Aug. 10, 2005.
Official Action corresponding to U.S. Appl. No. 10/829,137 dated Oct. 15, 2007.
Official Action corresponding to U.S. Appl. No. 11/663,126 dated Jul. 15, 2011.
Official Action corresponding to U.S. Appl. No. 12/221,956 dated Oct. 4, 2011.
Official Action corresponding to U.S. Appl. No. 12/221,956 dated Jun. 26, 2012.
Official Action corresponding to U.S. Appl. No. 13/012,433 dated Jul. 20, 2011.
Official Action corresponding to U.S. Appl. No. 13/012,433 dated Feb. 17, 2012.

* cited by examiner

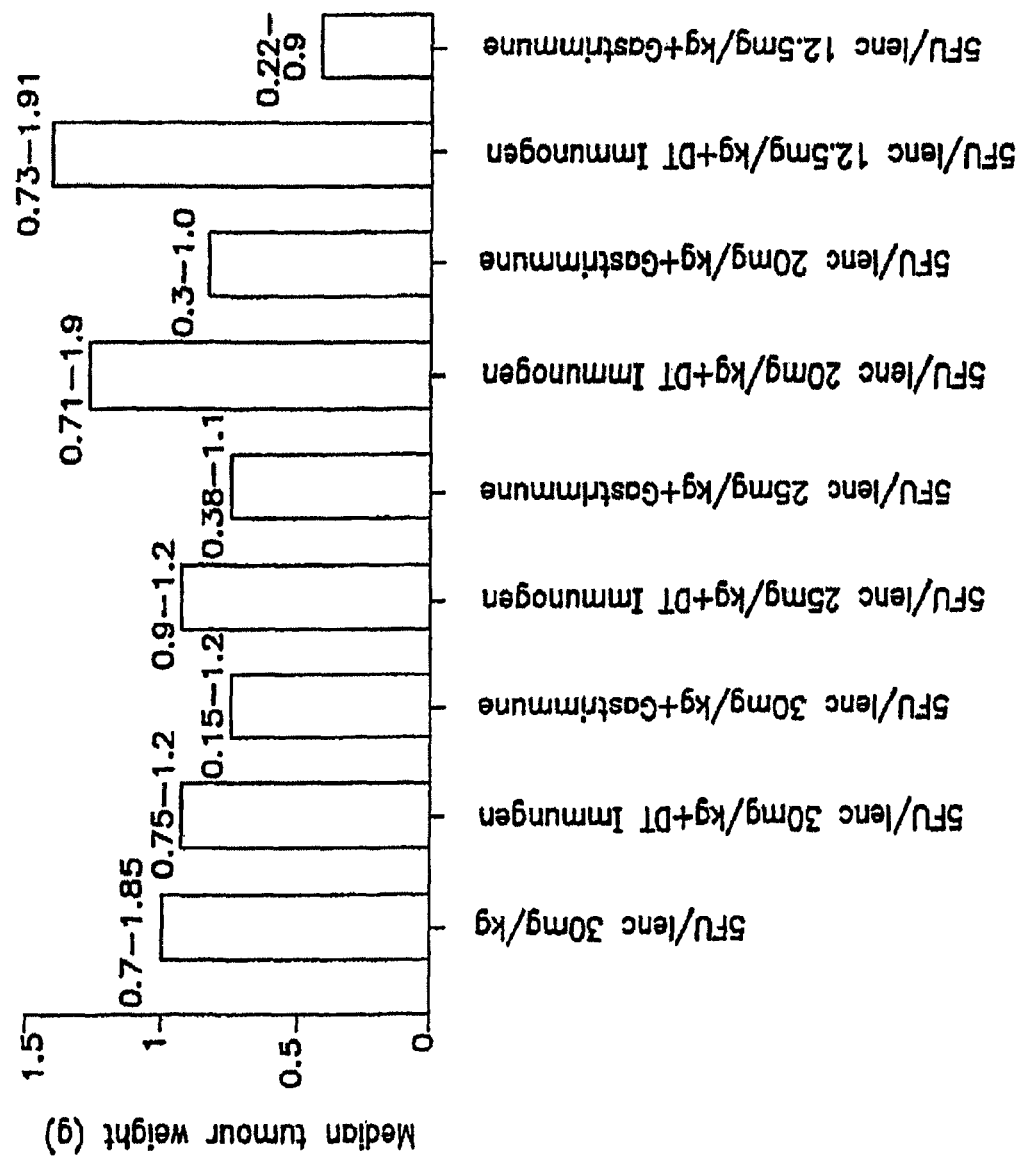

```
                        SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Human or synthetic peptide

<400> SEQUENCE: 1

Glu Gly Pro Trp Leu Glu Glu Glu Glu
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic peptide

<400> SEQUENCE: 2

Ser Ser Pro Pro Pro Pro Cys
1               5
```

COMBINATION THERAPY FOR THE TREATMENT OF TUMORS

CROSS REFERENCE TO RELATED APPLICATIONS

This application is a continuation of U.S. application Ser. No. 12/313,969 (abandoned), to Philip C. Gevas, Stephen Grimes, Stephen L. Karr, Susan A. Watson, and Dov Michaeli, filed on Nov. 25, 2008, entitled "COMBINATION THERAPY FOR THE TREATMENT OF TUMORS", which itself is a continuation of U.S. application Ser. No. 09/700,402 (abandoned), also to Philip C. Gevas, Stephen Grimes, Stephen L. Karr, Susan A. Watson, and Dov Michaeli, filed on May 4, 2001, entitled "COMBINATION THERAPY FOR THE TREATMENT OF TUMORS", which claims the benefit of priority under 35 U.S.C. §119(e) to U.S. Provisional Application Ser. No. 60/085,687 to Susan A. Watson and Dov Michaeli, filed on May 15, 1998. The subject matter of each of these applications is incorporated by reference in its entirety.

FIELD OF THE INVENTION

The invention is related to a tumor therapy for inhibiting growth by neutralizing immunologically the growth stimulating peptide hormones in combination with a chemotherapy apply a 5-fluorouracil derivative and leucovorin.

BACKGROUND OF INVENTION

Gastrin is a peptide hormone which occurs in two mature forms, tetratriacontagastrin (G34) and heptadecagastrin (G17), and is synthesized and secreted by specialized cells, G cells, that are located in the stomach antrum. In gastrin-producing cells, these gastrin hormones are posttranslationally processed from a common precursor molecule termed "preprogastrin" containing a signal peptide. The signal peptide "pre" is removed in the endoplasmic reticulum of the cell, resulting in the "progastrin" peptide, which is in turn further processed in the cell to yield the mature gastrins G34 and G17, before secretion into the bloodstream (Dickinson 1991). (The full citations for the references cited herein are provided in the Reference Section preceding the Claims): Both mature forms of G34 and G17 are amidated at their carboxy-terminal end ($-NH_2$). In humans, multiple forms of G17 have been found resulting from differential processing of the precursor molecule, each of which may have different biological activities (Dickinson 1995 and Ciccotosto et al. 1995). In the post-translational processing of gastrin, it is the "mature" carboxy-amidated form that binds to a specific cell receptor, the so-called CCK-B/gastrin receptor, via the carboxy terminus of the peptide (Kopin et al. 1992).

The gastrin hormones are secreted into the circulating blood and bind to specific cells in the stomach, namely, enterochromaffin-like (ECL) cells and parietal cells, that indirectly or directly affect stomach acid output. Historically, both gastrin hormones have been associated with the stimulation of gastric acid secretion (Edkins, J. S. 1905). In recent years, evidence has accumulated showing that gastrin also acts as a trophic factor within the gastrointestinal tract (Johnson, L. 1997) and that it promotes the growth of gastrointestinal cancers (Watson et al. 1989, Dickinson, C. J. 1995), as well as nongastrointestinal cancers, including small cell carcinoma of the lung (Rehfeld et al. 1989).

Several types of tumors, including colorectal, stomach, pancreatic and hepatocellular adenocarcinomas possess CCK-B/gastrin receptors in their plasma membranes and the tumor cells respond to gastrin- with powerful cellular proliferation (Rehfeld, J. F. 1972, Upp et al. 1989 and Watson et al. 1993). Elevated plasma levels of total gastrin occur in patients with colorectal cancers, and, in particular, increased amounts of the hormone precursor progastrin have been detected in many colorectal tumors using gastrin antisera (Ciccotosto et al. 1995). More recently, it has been discovered that many of these cancer cells also secrete gastrin and thus effect an autonomous proliferative pathway (Van-Solinge et al. 1993, Nemeth et al. 1993 and Seva et al. 1994).

The peptide hormones G17 and G34 bind to the CCK-B/gastrin receptors on the cell membranes of normal cells. However, it has been found that G17, but not G34, stimulates the growth of gastrin-dependent cancer cells. Serum-associated G17, in particular, has the potential to stimulate the growth of colorectal tumors in an .endocrine manner mediated by CCK-B/gastrin receptors in tumor cells (Watson et al. 1993). G17 is particularly implicated in stimulating the growth of colorectal adenocarcinomas due to a possible increased affinity for the CCK-B/gastrin receptors on the tumor cells, as compared to other gastrin hormone species (Rehfeld 1972 and 1993). The CCK-B/gastrin receptors were found to be expressed in a high affinity form on 56.7% of human primary colorectal tumors (Upp et al. 1989).

Numerous studies have shown that, in addition to being able to respond to exogenous endocrine gastrin, human gastric and colorectal tumors produce gastrin and its precursors (Ciccotosto et al., 1995; Finley et al., 1993; Kochman et al., 1992; Nemeth et al., 1993; Van Solinge et al., 1993), thus effecting an autocrine growth stimulatory pathway. Gastrin production in tumor cells differs from that of endocrine G cells. Specifically, those tumor cells contain a high proportion of the precursor progastrin along with a lower concentration of mature peptides. This abnormal ratio is postulated to be due to constitutive unregulated release of gastrin combined with a limited activity of peptidylglycine α-amidating monooxygenase (Ciccotosto et al., 1995; Kelly, 1985). Thus, the unregulated release of gastrin leads to the abnormal production and secretion of different molecular forms of the hormone. Specifically, colon carcinoma cells do not efficiently process progastrin resulting in less conversion of precursor gastrin to the mature peptides and, thus, produce mostly incomplete or aberrant gastrins, (Dickinson 1993 and Rehfeld et al. 1993). In addition, the increased gastrin level in colorectal tumors is, in part, attributed to the aberrant expression of the gastrin gene in the colorectal tumor cells (Hoosein et al. 1990, Baldwin et al. 1992 and Finley et al. 1993). Gastrin-like peptides have been identified in such cells (Hoosein et al. 1988, Watson et al. 1991 and Finley et al. 1993), and were confirmed to be precursor gastrin species (Van-Solinge et al. 1993 and Nemeth et al. 1993).

The presence of amidated G17 ($G17-NH_2$) in some colorectal cancers (Ciccotosto et al., 1995; Van Solinge et al., 1993) demonstrates that some tumors retain an intact processing pathway, as gastrin amidation only occurs in secretory granules (Varro et al, 1994). Endogenously produced gastrin also acts as an autocrine growth factor, since the basal growth of a colorectal cell line was shown to be inhibited by an anti-gastrin antibody (Hoosein et al., 1988). This was confirmed in a second study in which Northern blot analysis revealed gastrin mRNA in the same cell lines and radioimmunoassay revealed gastrin-like immunoreactivity in cell culture supernatant (Hoosein et al., 1990).

Gastrin peptides also possess paracrine roles (Watson et al., 1991b) which was confirmed (Finley et al., 1993) in experiments showing gastrin immunoreactivity more predominant in subpopulations of malignant colorectal mucosal cells.

When G17 binds to its receptor a G17/receptor complex is formed which stimulates cell growth by way of secondary messengers for regulating cell function (Ullrich et al. 1990). The binding of G17 to the CCK-B/gastrin receptor leads to activation of phosphatidylinositol breakdown, the protein kinase C activation with a resultant increase in intracellular calcium ion concentration, and the induction of c-fos and c-jun protooncogenes via the mitogen-activated protein kinase, which has been implicated in the regulation of cell proliferation (Tadisco et al. 1995). Additionally, gastrin binding to the CCK-B/gastrin receptor has been associated with the subsequent increase in phosphorylation by a tyrosine kinase, the pp125FADK (focal adhesion kinase), which may also have a role in the transmission of mitogenic signals (Tanaguchi et al. 1994).

Colorectal cancer remains a formidable disease to treat, as only minor improvements in survival have been obtained in recent years. Surgery is an effective treatment of the primary disease, but it is ineffectual against residual occult disease, which is frequently present. Radiation therapy post-surgery is generally recommended for patients with rectal cancers to reduce the risks of recurrence of the disease. Chemotherapy with 5-fluorouracil (5-FU) has been the most traditional effective therapy following surgery in patients with more advanced colorectal cancers. However, 5-FU therapy has been shown to be only of marginal benefit to the patient, since 5-FU is highly toxic and the therapy is costly and does not appear, alone or in combination with other cytotoxic drugs, to significantly prolong survival. In most instances, occult or inoperable colorectal tumors do not respond well to chemotherapy or radiation, and new treatments are needed to supplement present procedures.

Recently, several studies have shown that adjuvant combination chemotherapy with 5-FU and Leucovorin improves the efficacy of 5-FU in patients with advanced colorectal cancer. Leucovorin is a folic acid -derivative, also known as folinic acid, Citrovorum factor, or 5-formyl-5,6,7,8,-tetrahydrofolic acid. The studies show that in Dukes' stage C patients, 5-FU/Leucovorin combination therapy may reduce mortality by 10 to 15% (Moertel, 1994). In the same patient group, combined intravenous and intraperitoneal therapy with 5-FU/leucovorin resulted in a non-significant trend to disease-free survival and overall survival advantage (Scheithauer et al., 1995). In advanced disease, the same drug combination may give rise to a survival advantage (Taylor, 1993), which has been shown to be 13.5 months of median survival in the" combination group compared to 7.5 months in 5-FU-treated patients (Petrioli et al., 1995). However, this combination chemotherapy is not without significant morbidity and causes deleterious side effects including stomatitis, diarrhea and myelosuppression (Mahood et al., 1991; Erlichman et al., 1988; Pietnelli et al., 1989), making quality of life an issue, especially in patients with advanced disease.

A number of high affinity CCK-B/gastrin receptor antagonists have been evaluated therapeutically both in vitro and in vivo in a number of experimental gastrointestinal cancers. For example, proglumide, a glutamic acid derivative (Seva et al. 190; Harrison et al. 1990 and Watson et al. 1991a); Benzotript, an N-acyl derivative of tryptophan; L-365,260, a derivative of Aspercillin (Bock et al. 1989); and CI-988, a molecule that mimics the C-terminal pentapeptide sequence of CCK (Hughes et al. 1990), have been shown to effectively neutralize the effects of exogenous gastrin on gastrointestinal tumor growth both in vitro and in vivo (Watson et al. and Romani et al. 1994). However, these antagonists have severe toxic side effects and lack specificity, as they block the action of all potential ligands of the receptor such as G34 and CCK in normal cells. Recently, highly potent and selective CCK-B/gastrin receptor antagonists such as YM022 (Yuki et al., 1997) and YF476 (Takinaini et al., 1997) have been also described.

Proglumide and Benzotript have been widely assessed in preclinical studies. The main problem with these compounds is their lack of potency, with relatively high concentrations required to displace G17 (Watson et al., 1992a; Watson et al., 1992b).

Despite this, proglumide and Benzotript inhibited the basal and gastrin-stimulated proliferation of a number of cell lines (Seva et al., 1990; Watson et al., 1991a). In addition, proglumide increased the survival of xenograft mice bearing the gastrin-sensitive mouse colon tumor MC26 to 39 days in the treated animals from 25 days in the control animals.

Due to the low specificity of this class of gastrin antagonizing agents for the gastrin/CCK-B receptor, the inhibition of growth is also thought to be induced by a gastrin-receptor-independent action. Moreover, the cellular receptors which recognize and bind the gastrin do not bind all the inhibitors tested (Seva et al. 1994). Thus, if complete inhibition of gastrin binding to the receptor does not occur in the autocrine growth cascade, the gastrin antagonists may be unable to block this mechanism of tumor growth promotion.

Thus, novel therapeutic approaches are needed both as modalities in their own right and for combination strategies with chemotherapy. Combined treatments offer the possibilities of enhancing the therapeutic index and/or reducing the dose of chemotherapy required, thereby limiting the disadvantageous side effects.

A therapeutic method of selectively immunologically neutralizing the biological activity of the gastrin hormone would provide an effective means of controlling or preventing the pathologic changes resulting from excessive gastrin hormone production associated with colorectal cancers.

Coassigned U.S. Pat. Nos. 5,023,077; 5,468,494; 5,607,676; 5,609,870 and 5,622,702 disclose immunogens and immunogenic compositions useful for controlling G17 and G34 levels in a patient by generating anti-gastrin antibodies and also disclose the use of such compositions for the treatment of gastric and duodenal ulcers and gastrin-induced cancers. The present invention concerns the use of the anti-G17 immunogens and immunogenic compositions disclosed in U.S. Pat. Nos. 5,023,077; 5,468,494; 5,607,676; 5,609,870 and 5,662,702 in a combination therapy with chemotherapeutic agents for treating gastrin-dependent colorectal cancers.

The method of cancer therapy described herein has several advantages over present colorectal cancer treatment methods. The anti-G17 immunization, in combination with chemotherapeutic agents such as 5-FU and Leucovorin, increases the therapeutic effects in controlling or inhibiting colorectal tumor growth over chemotherapy alone.

SUMMARY OF THE INVENTION

The present invention provides a combination therapy for treating tumors comprising immunologically neutralizing peptide hormones and factors which promote tumor cell division in combination with chemotherapy. In particular, the present invention provides a method for treating gastrin-dependent cancers, such as colorectal adenocarcinomas. The method comprises a combination therapy comprising anti-G17 immunization of the patient in need of the therapy, in conjunction with the administration of one or more chemotherapeutic agents. The anti-G17 immunization for treating gastrin-dependent tumors is surprisingly effective in generating anti-G17 antibodies, despite the known myelo-suppressive effects of the chemotherapeutic agents used.

The anti-G17 immunization comprises the active or passive immunization of a patient with an anti-G17 immunogen against the hormone G17 in order to control the patient's G17 levels. As the result of induction of anti-G17 antibodies in a patient, the G17 hormone is neutralized in vivo and its physiological effects are inhibited, thereby inhibiting G17-dependent tumor cell growth.

Furthermore, the use of anti-G17 immunization in combination with standard chemotherapy increases the efficacy of colorectal cancer treatment, since in the combination, lower amounts of chemotherapeutic agents may be required to treat a patient, thereby lowering their toxic effects on normal tissues. In addition, the patient's quality of life may be improved and his survival time prolonged.

In a preferred embodiment, the method comprises the active immunization of a mammal possessing a gastrin-dependent tumor with an anti-G17 immunogen, in combination with the administration of one or more chemotherapeutic agents, such as 5-fluorouracil, leucovorin, levamisole, cisplatin, tumor necrosis factor and proglumide. The anti-G17 immunogen may be administered to a patient at the onset of therapy and at subsequent intervals as required by the patient. The anti-G17 antibodies produced by the patient following immunization bind and neutralize G17 in its mature, amidated-G17 as well as its precursor forms, e.g., G17-Gly, in vivo and prevent the binding of G17 to its receptors, thereby preventing gastrin-dependent tumor cell growth. The anti-G17 antibody titers produced by an immunized patient may be monitored at predetermined intervals using standard techniques. In addition, the chemotherapeutic agents may be administered as directed by standard regimes or lower doses may be administered as required by the patient.

In another embodiment, the invention further provides a method of treating a gastrin-dependent tumor comprising the passive immunization of a patient possessing a gastrin-dependent tumor with anti-G17 antibodies in combination with one or more chemotherapeutic agents, such as 5-fluorouracil, leucovorin, levamisole, cisplatin, tumor necrosis factor and proglumide. In a preferred embodiment of this aspect of the invention, the antibodies may be chimeric, humanized, or human monoclonal antibodies which may be produced by methods well known in the art. The antibodies may be administered together with the chemotherapeutic agents at the onset of therapy and at subsequent intervals after the initial therapy, as required by the patient.

BRIEF DESCRIPTION OF THE DRAWINGS

FIG. 5 depicts a bar graph showing the median tumor weights of rats treated with 30 mg/kg of 5-FU/leucovorin; 30 mg/kg of 5-FU/leucovorin and DT immunogen; 30 mg/kg of 5-FU/leucovorin and anti-G17(1-9)-DT; 25 mg/kg of 5-FU/leucovorin and DT immunogen; 25 mg/kg of 5FU/leucovorin and anti-G17(1-9)DT; 20 mg/kg of 5-FU/leucovorin and DT immunogen; 20 mg/kg of 5-FU/leucovorin and anti-G17(1-9)DT; 12.5 mg/kg of 5-FU/leucovorin and DT immunogen; and 12.5 mg/kg of 5-FU/leucovorin and anti-G17(1-9)DT.

DETAILED DESCRIPTION OF THE INVENTION

Figure 1:
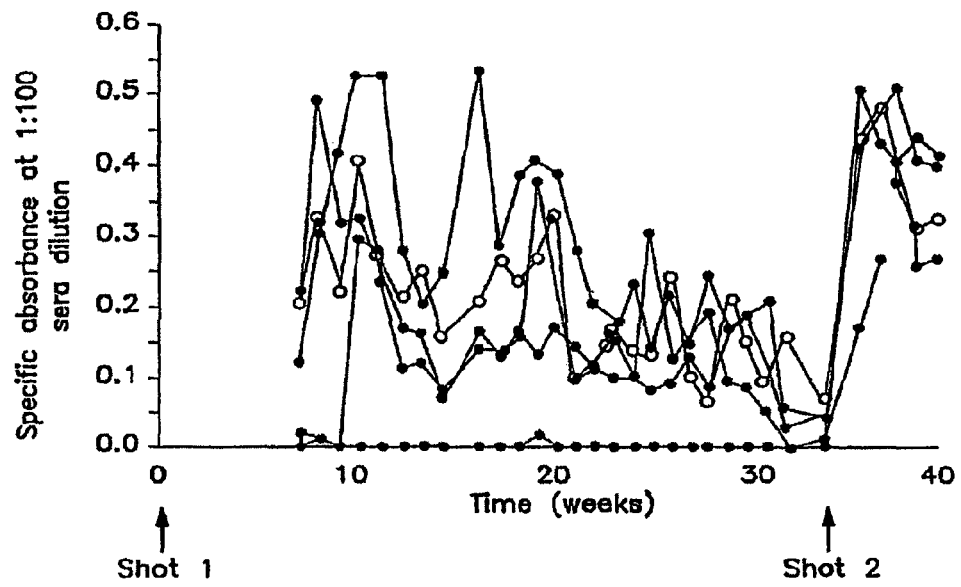
FIG. 1 depicts a graph showing a time scale of serum antibody titers after immunization of rats immunized with 500 μg/ml of rat anti-G17 (1-9)-DT immunogen.

The present invention provides methods of treating tumors, in particular those associated with gastrin-dependent colorectal cancer, with a combination therapy comprising immunizing a patient with an anti-G17 immunogen and treating the patient with chemotherapeutic agents, such as 5-FU and leucovorin. The anti-G17 immunization/5-FU-leucovorin combination therapy, surprisingly, has been found to be more effective than previous therapies in treating colorectal cancer. The chemotherapeutic agents useful in the combination therapy do not significantly inhibit anti-G17 antibody production in an immunized patient and lower doses of chemotherapeutic agents can be used for treating the tumor growth. In addition, the anti-G17 antibody titers produced by immunization are effective to neutralize all forms of G17 hormone.

In a preferred embodiment, the method comprises actively immunizing a patient afflicted with a gastrin-dependent colorectal cancer applying an anti-G17 immunogenic composition in conjunction with administering to the patient chemotherapeutic agents. Subsequent booster anti-G17 immunizations may be administered as required by the patient, as determined-by analysis of the patient's serum anti-G17 antibody titers post-immunization, using standard techniques and standard radiological assessments of the tumors. Anti-G17 immunization may also be provided to a patient prior to tumor surgery.

The anti-G17 immunogens comprise a natural or synthetic peptide fragment of the N-terminal amino acids of G17 as the immunomimic portion of-the immunogen. This peptide fragment is conjugated to an immunogenic carrier such as Diphtheria toxoid (DT). In a preferred embodiment of this aspect of the invention, the anti-G17 immunogen comprises the amino-terminal amino acids of G17 from positions 1 through 9, having the amino acid sequence pyroGlu-Gly-Pro-Trp-Leu-Glu-Glu-Glu-Glu (SEQ ID NO: 1), conjugated to Diphtheria toxoid. Other suitable immunogenic protein carriers, include bovine serum albumin, keylimpet hemocyain, hemocyanin and tetanus toxoid.

The immunogens of the invention may also comprise an extension or a spacer peptide sequence-suitable for projecting the immunomimic peptide away from the protein carrier and for enhancing its capacity to bind the -lymphocyte receptors. A suitable spacer peptide sequence is the amino acid sequence SSPPPPC (SEQ ID NO: 2 in the Sequence Listing). However, other spacer peptides would be suitable as well. In a preferred embodiment of this aspect of the invention, the preferred spacer sequence is attached to the carboxy-terminal end of the immunomimic peptide. The immunogens of the invention are produced by standard techniques and are disclosed in U.S. Pat. Nos. 5,023,077; 5,468,494; 5,607,676; 5,609,870; 5,688,506 and 5,662,702, the disclosures of which are hereby incorporated by reference. Following immunization, the immunogens of the invention produce high affinity, neutralizing antibodies for inhibiting the effects of G17 in its mature and precursor forms on tumor growth in immunized animals. The anti-G17 antibodies produced bind and neutralize mature and precursor G17, thereby preventing the binding of G17 to the receptors on tumor cells and ultimately inhibiting tumor cell growth. The immunogens raise antibodies which neutralize both the carboxy-amidated and glycine-extended G17, and show no cross-reactivity with G34 or CCK.

The compositions in which the immunogens for active immunization are administered for the treatment of gastrin-dependent tumors in patients may be in a variety of forms. These include, for example, solid, semi-solid and liquid dosage forms, such as powders, liquid solutions, suspensions, suppositories, and injectable and infusible solutions. The preferred form depends on the intended mode of administration and therapeutic applications. The compositions comprise the present immunogens and suitable pharmaceutically acceptable components, and may include other medicinal agents, carriers, adjuvants excipients, etc., which can be mixed using standard procedures. Preferably, the compositions are in the form of unit doses. The amount of active compound administered for immunization or as a medicament at one time, or over a period of time, will depend on the subject being treated, the manner and form of administration, and the judgment of the treating physician.

An effective dosage ranging from 0.001 to 2 mg of the immunogenic composition is administered to the patient for the treatment of the gastrointestinal cancer. The effective dosage of the immunogenic composition is capable of eliciting an immune response in a patient of effective levels of antibody titer to bind and neutralize mature and precursor G17 for 1-3 months after immunization. Following the immunization and the chemotherapeutic agent treatment, with, for example, 5-FU/Leucovorin, of a patient with colorectal cancer, the effectiveness of the therapy on tumor growth is assayed by standard clinical procedures, such as ultrasound and magnetic resonance imaging (MRI) to detect the presence and size of tumors, if any. The anti-G17 antibody titers may also be monitored from a sample of blood taken from the patient.

Booster immunizations should be given as required to maintain an effective antibody titer. Effective treatment of gastrin-dependent colorectal adenocarcinoma and other gastrin-dependent cancers such as stomach, liver, pancreatic and small cell carcinoma of the lungs according to this method should, result in inhibition of tumor growth and a decrease in size of the tumor.

For passive immunization, the anti-G17 antibodies are administered to a patient intravenously using a pharmaceutically acceptable carrier, such as saline solution, for example, phosphate-buffered saline.

The chemotherapeutic agents are administered at doses recommended in standard regimes and may be administered at the onset of therapy simultaneously with anti-G17 immunogen, prior to immunization or after immunization. In some cases, it may be beneficial to administer the chemotherapeutic agent both before and after immunization. Subsequent chemotherapeutic treatments may also be administered as required by the patient following evaluation by MRI and ultrasound imaging.

The following experiments were conducted to demonstrate the effects of the present combination therapy on colorectal cancers.

EXAMPLE 1

The following experiments were conducted to determine the potential clinical benefit offered by anti-G17(1-9)-DT. The aims of this study were as follows:

(a) to determine the long term effect of specific rat anti-G17(1-9)-DT immunization on the histological appearance of the rat GI tract.

(b) to evaluate the effect of 5-FU/Leucovorin combinations on antibody titers raised by anti-G17(1-9)-DT; and (c) to determine the therapeutic effect of anti-G17(1-9)-DT and 5-FU/leucovorin combinations on a rat colon model.

Cell line. DHDK12 is a rat colonic epithelial tumor cell line (Martin, 1983). The cell line was maintained in RPMI 1640 growth medium (Gibco, Paisley, Scotland) containing 10% fetal calf serum (FCS, Sigma, Poole, UK) in humidified conditions at 37° C. and 5% $CO_2$.

Immunogen. The anti-G17(1-9)-DT immunogen consists of amino acid residues 1-9 of G17 linked via the carboxy-terminus to the peptide spacer SSPPPPC (SEQ ID NO: 2 in the Sequence Listing), which in turn is conjugated to DT. The immunogen used in these studies was made specific for rat G17 by replacing the human G17 epitope with the amino terminal 9 amino acids of rat G17; linked through a peptide spacer to diphtheria toxoid (DT). Antiserum raised by rat anti-G17(1-9)-DT was denoted as anti-rat G17 (1-9):DT.

Experimental animals. Male and female BDIX rats were provided by the Cancer Studies Unit, University of Nottingham, UK and were 6-10 weeks old, weighing 340-420 g. The rats were housed in pairs and maintained in a cycle of 12-hour light and 12-hour dark at 25° C. with 50% humidity.

Prior to each experiment, the animals were grouped to equalize weight distribution. Group sizes ranged from 6-13 animals. The UK Coordinating Committee for Cancer Research (UKCCCR) guidelines were adhered to throughout all animal experimentation.

Immunization procedure. Rat anti-G17(1-9)-DT was dissolved in sterile saline (0.9%), pH 7.3 to 1 mg/ml. The adjuvant, nor-muramyl dipeptide (Peninsula Labs., Belmont, Calif., USA), was added to the conjugate solution to give a final conjugate concentration of between 200 and 500 µg/ml. The aqueous solution was formulated with an oily vehicle (montanide ISA 703; AMS Seppic Inc., Paris, France) in a 1:2 ratio (v/v) by emulsification. After placing in a glass syringe which was attached to a second syringe through a three-way stopcock, the mixture was forced back and forth through the syringes 40 times to form an emulsion. An emulsion containing DT peptide and muramyl dipeptide was similarly formulated for control rats. A 200 µl volume of emulsion (50 µg/rat) was injected s.c. (right- hand-flank of the-experimental-animals). The animals were immunized with either a single injection or repeatedly at 21 day intervals as detailed below.

Cytotoxic treatment regime. Rats received 12.5 and 25 mg/kg of 5-Fluorouracil (5-FU, David Bull Labs., Warwick, UK) and 12.5-25 mg/kg Leucovorin (Lederle Labs., Gosport, Hants, UK) administered intravenously (iv) on days 1, 3 and 5 with the cycle being repeated every 4 weeks over the duration of the study period (Asao, 1992). The cytotoxic combination was administered to the rats either prior to or after anti-G17(1-9)-DT immunization (200 µg/ml).

Initiation of tumor growth. DHDK12 cells were suspended in sterile phosphate buffered line (PBS, Oxoid, Hants., UK) at a cell concentration of $2.5 \times 10^7$/ml. Rats were anesthetized by a 1 ml intraperitoneal injection of Hypnorm (0.315 ng/ml fenatanyl citrate and 10 mg/ml fluanisone; Jannsen, Berrse, Belgium), Hypnovel (5 ng/ml midazolam; Roche, Basel, Switzerland), and sterile distilled water in a 1:1:5 ratio. Following a subcutaneous (s.c.) incision on the right flank, a 200 µl volume of cell suspension was injected into the muscle layer of the abdominal wall and the surgical incision closed by wound clips. Each experimental group was composed of between 6 and 13 animals.

Determination of specific antibody levels of rat anti-G17 (1-9)-DT-immunized rats. To obtain blood samples for analysis, rats were tail-bled at various time points throughout the experiment and at termination by cardiac puncture under terminal anesthesia. Serum anti-rat-G17 antibody levels were determined by enzyme-linked immunosorbent assay (ELISA). A rat G17-bovine serum albumin (BSA) conjugate was dissolved to 2 μg/ml in 0.1M glycine buffer (pH 9.5) and 25 μl per well was plated into 96-well Immunulon U plates (Dynatech Labs., Sussex, UK). The wells were incubated overnight at 4° C. after which the unadsorbed conjugate was flicked out and the wells were washed with buffer (0.9% saline, 0.5% Tween-20 [Sigma], 0.02% $NaN_3$ [Sigma], pH 7.3). This buffer was used for all washing steps and reagent dilutions. Sera were treated at 10-fold serial dilutions, starting at a dilution of 1:100. The positive control was rat anti-rat G17(1-9)-DT antiserum from previously immunized animals and the negative controls were normal rat serum, and serum from rats immunized with DT only. All control sera were used at the same dilutions as the test sera. The diluted sera were added to the wells in 25 μl aliquots in the presence or absence of 25 μl/well rat G17-BSA at 100 μg/ml (as a soluble inhibitor). Baseline control wells received 25 μl assay buffer only. The plates were incubated for 60 minutes. at room temperature before washing with the assay buffer. Goat anti-rat immunoglobulin (H+L)-biotin (Zymed; San Francisco, Calif., USA) was added to the wells at a 1:500 dilution, 50 μl/well and incubated for 60 minutes. in the dark at room temperature. After washing, avidin-alkaline phosphatase (Zymed), 1:100 dilution was added (50 μl/well) and the plates were incubated for 60 mins. at room temperature. After further washing, ρ-nitrophenylphosphate (pNPP) substrate (Sigma) was added to the wells at 50 μl/well and after a 5-minute developing time, the absorbance was read at 405 nm. The difference in absorbance between untreated sera and sera co-incubated with rat G17-BSA was calculated as the specific absorbance.

Determination of white blood cell counts. Heparinized blood from the rats was collected by tail bleeds during the experiment and by cardiac puncture at the termination of the experiment. The numbers of white blood cells were analyzed by the Hematology Department at the University Hospital, Nottingham with the use of a FACScan.

Histology. At termination of the long-term anti-G17(1-9)-DT-immunized: rats, representative areas of the stomach, colon and rectum from the immunized rats and age-matched controls were dissected and formalin-fixed. The sections were then embedded in paraffin and 4 μm sections were cut by use of a microtome. These were stained by hematoxylin and eosin and evaluated by a histopathologist who had no knowledge of the treatment groups.

Crypt cell proliferation rate. One hour prior to animal termination, vincristine (2 mg/kg, Sigma) was injected intraperitoneally to induce metaphase arrest in the colonic epithelium prior to the assessment of colonic crypt cell proliferation (CCPR). The number of cells in metaphase per crypt were counted. The colon and rectum were removed from each rat, opened longitudinally and mucosa from each fixed in Carnoys' solution. Crypts were gently squashed, longitudinally, under a dissecting microscope and the number of cells in metaphase enumerated (magnification ×25).

Statistical analysis. In vivo results were analyzed by a Mann Whitney non-parametric test by use of the SPSS statistical package for the IBM PC.

Long term anti-G17(1-9)-DT studies. Five male rats were immunized with rat anti-G17(1-9)-DT immunogen as described above, and their antibody titers were measured for a period of 34 weeks following a single immunization. At this point; the rats were boosted with a second injection of rat-anti-G17(1-9)-DT. The results are shown in FIG. 1. FIG. 1 shows the time-scale up to 40 weeks after immunization of antibody titers from rats immunized with 500 μg/ml of rat anti-G17(1-9)-DT. Each point represents an individual animal. Antibody titers were measured by an ELISA assay as described above using a 1:100 dilution of sera. Immunizations are indicated by the arrow. Following the primary immunization, 4 of the 5 rats responded to the rat anti-G17 (1-9)-DT immunogen. Antibodies, following this single injection, were detectable by week 7 in 3 of 5 rats and in 4 of 5 rats by week 9. This initial surge of antibodies was followed by a second surge between 15-20 weeks, after which the antibody titers steadily declined and were approaching zero by week 34. At this point, FIG. 1 also shows that after a second immunization with rat anti-G17(1-9)-DT, all rats had detectable anti-rat-G-17 antibody titers within 1-2 weeks post-immunization.

EXAMPLE 2

Histological Analysis of the Long Term Anti-G17(1-9)-DT-immunized Rats

Specimens from the stomach, colon and rectum were evaluated histologically following hematoxylin and eosin staining as described in EXAMPLE 1. These were compared to specimens from age and sex-matched control rats. All areas of the GI tract evaluated were identical in both anti-G17(1-9)-DT-treated and age-matched control rats with respect to length of villae/crypts/mucosal height. In the stomach, enterochromaffin-like (ECL) cells were similar in number and appearance in the two subject animal groups. However, there was some evidence of granulation of the G cells in the anti-G17(1-9)-DT-treated rat stomach mucosa.

EXAMPLE 3

Crypt Cell Proliferation Rate (CCPR) of Colonic Epithelium from Long Term Anti-G17(1-9)-DT-Immunized Rats The CCPR of colonic epithelium and anti-rat G17-antibody titers were analyzed as described above. Table I shows the results obtained from 4 of 5 rats evaluated comparing CCPR to anti-rat G17 antibody titers. The mean CCPR for control rats was 18.93 (standard deviation 3.2) and for the anti-G17(1-9)-DT-immunized rats 23.7 (standard deviation 7.9). There was no statistical difference in CCPR between the anti-G17(1-9)-DT-immunized and age-matched control rats. These results indicate that the rate of crypt cell division in a colonic epithelium is the same for control and anti-G17(1-9) DT-immunized rats.

TABLE I

A Comparison of Anti-rat G17:DT Antibody Titers with the Crypt Cell Proliferation of the Colon

| Rat | Specific absorbance relating to anti-rat G17:DT antibodies (1:1000 dilution) | Crypt cell proliferation rate (mean metaphases/crypt after 2 hours vincristine treatment) |
| --- | --- | --- |
| Control 1 | 0 | 21.9 |
| Control 2 | 0 | 19.4 |
| Control 3 | 0 | 14.4 |
| Control 4 | 0 | 20.0 |
| Immunized rat 1 | 0.280 | 29.7 |
| Immunized rat 2 | 0.340 | 30.3 |
| Immunized rat 3 | 0.415 | 13.6 |
| Immunized rat 4 | 0.420 | 21.1 |

EXAMPLE 4

Effect of Pre- and Post-cytotoxic Treatment on Antibody Levels Raised by Rat Anti-G27(2-9)-DT Rats were injected intravenously with a 1:1 ratio of 5-FU/Leucovorin at 30 mg/kg as described in Example 1 prior to or after anti-G17(1-9)-DT immunization. Each group consisted of 6 male and 6 female rats per group and the mean antibody titers were measured by an ELISA technique using a 1:100 dilution of sera. Antibody levels in each rat were measured from blood samples as described in Example 1.

Figure 2:
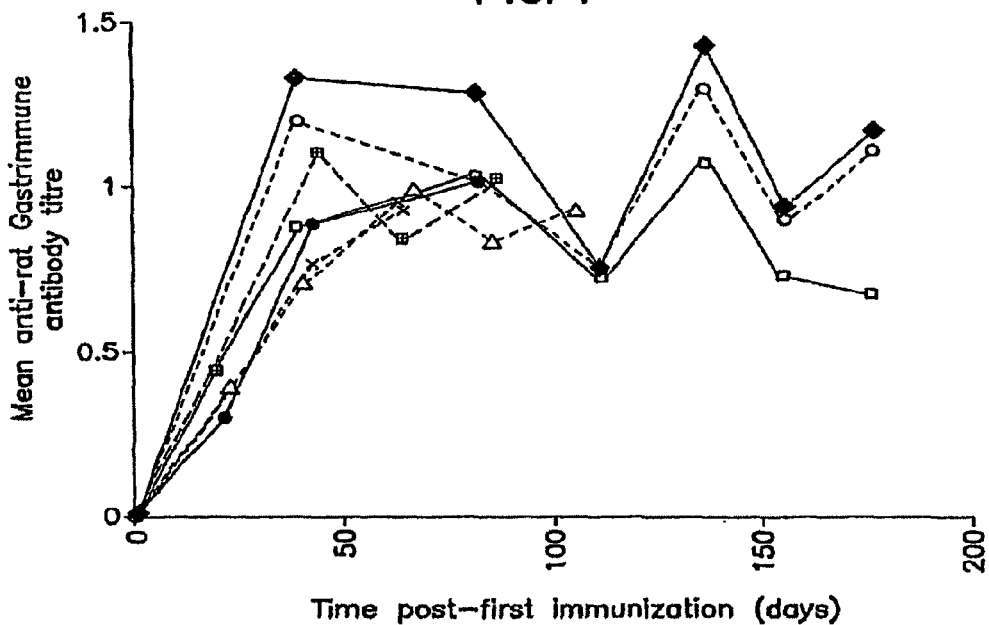
FIG. 2 depicts a graph showing the effects of 30 mg/kg dose of 5-FU/leucovorin treatment on the anti-G17(1-9) antibody titers obtained in rats immunized with the immunogen of the invention.

FIG. 2 shows the effect of pre- and post-cytotoxic treatment with 30 mg/kg of 5-FU/Leucovorin cycles on antibody titers raised by anti-G17(1-9)-DT immunization (500 μg/ml). In the figure, the data is represented as follows: —□— no cytotoxics, 7 immunizations; —♦—2 immunizations prior to 4 cytotoxic treatments; —○— 1 immunization prior to 4 cytotoxic treatments; —Δ— 1 cytotoxic prior to 4 immunizations (2 cytotoxic treatments during immunizations); —⊞—2 cytotoxic treatments prior to 4 immunizations; —*—3 cytotoxic treatments prior to 3 immunizations; and —●—4 cytotoxic treatments prior to 2 immunizations.

FIG. 2 shows the mean of 6 female and 6 male rats per group. The standard deviations were around 10% of the mean. There was no significant effect on antibody titers by pre-treatment with cytotoxic 5-FU/Leucovorin combination on either the antibody levels achieved or the time taken to achieve those levels when compared to untreated anti-G17(1-9)-DT-immunized rats. The maximum number of treatment cycles evaluated was 4 cytotoxic treatment cycles followed by 2 immunizations.

Figure 3:
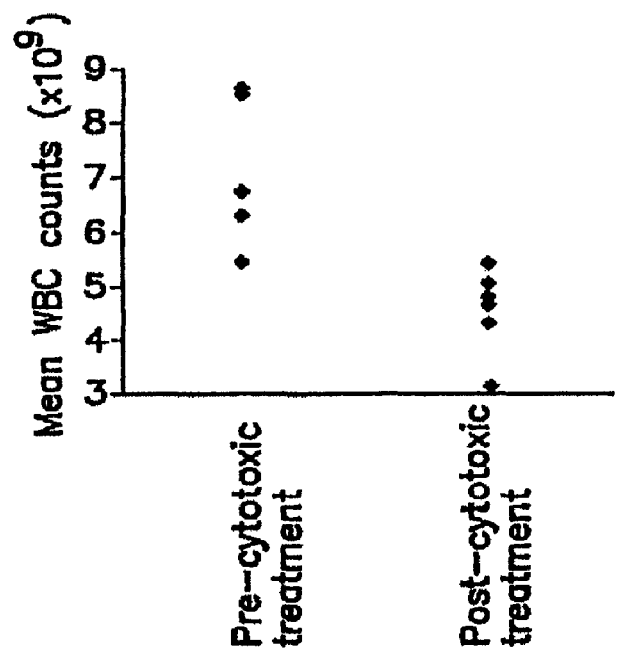
FIG. 3 depicts a Scatchard plot showing the effects of treatment cycles of 30 mg/kg of 5-FU/leucovorin on the mean white blood cell counts in BDIX rats.

FIG. 3 shows the effects of treatment on mean white blood cells (WBC) counts, in BDIX rats.

The effect of cytotoxic treatment with 30 mg/kg 5-FU/Leucovorin in BDIX rats receiving 4 cytotoxic treatments prior to 2 immunizations on the mean white blood cell (WBC) counts is shown in FIG. 3. As shown in the figure, there was a significant reduction in WBC counts in the representative rats evaluated, post cytotoxic treatment ($p<0.005$, Students' t-test). The counts were reduced by the number of cytotoxic treatment cycles, indicative of some myelosuppression. However, there was no effect on the antibody response to anti-G17 (1-9)-DT produced by the rats, as shown in FIG. 2.

EXAMPLE 5

Effect of Combination Therapy of 5-FU/Leucovorin and Anti-G17(1-9)-DT on the In Vivo Growth of DHDK12 Tumors The effects of combined therapies with 5-FU/Leucovorin (12.5-30 mg/kg) and rat anti-G17(1-9)-DT (200 μg/ml) on the growth of the rat colon tumor DHDK12 cell line in the muscle layer of the abdominal wall of BDIX rats were tested by comparison to tumors in control animals as described in the previous Examples. At the end of the therapies the rats were killed, their tumors excised and weighed using standard procedures. Each group consisted of 10-12 rats/group of mixed sex. The median tumor weights are shown with the interquartile ranges above the columns. Statistical assessment was done by a Mann Whitley U non-parametric test as described in Example 1.

Figure 4:
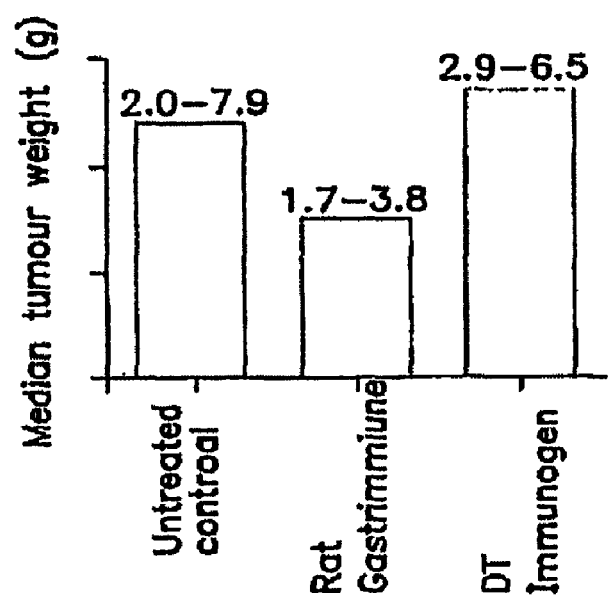
FIG. 4 depicts a bar graph showing the median tumor weight of untreated, anti-G17(1-9) DT-treated AND DT-treated rats.

FIGS. 4 and 5 show the effect of anti-G17(1-9)-DT immunization on the median final tumor weights from BDIX rats implanted with DHDK12 tumor cells in the muscle layer of the abdominal wall. This route of implantation results in a well-vascularized tumor amenable to therapies administered into the circulation (Watson, 1996). Rat anti-G17(1-9)-DT had previously been shown to inhibit final DHDK12 tumor weight by 56.5% when administered at a dose of 500 μg/ml (Watson, 1996). In the present experiments, to detect any benefits of combination therapy with 5-FU/Leucovorin, the anti-G17(1-9)-DT dose was dropped to 200 μg/ml, which resulted in a significant inhibition of tumor growth of 25.7% as shown in FIG. 4. FIG. 4 shows data from tumors excised from untreated control rats, anti-G17(1-9)-DT immunized rats and DT-immunized rats. After a 50 day time period untreated rats had a mean tumor weight of 4.43 g. DT immunization resulted in a median tumor weight of 4.7 g, which was not significantly different from the tumor weights of untreated rats, but which was significantly greater than the median tumor weight of anti-G17(1-9)-DT-immunized rats (3.49 g, $p=0.034$, Mann Whitney).

FIG. 5 shows that 5-FU/Leucovorin alone, given at 30 mg/kg, significantly reduced tumor weight to a median of 1.01 g ($p=0.0106$ when compared to untreated control rats). When rats were treated with the same cytotoxic dose of 5-FU/Leucovorin together with DT immunization, the median tumor weight was not significantly different (0.945 g).

A combination of 5-FU/Leucovorin at 30 mg/kg and rat anti-G17(1-9)-DT immunization resulted in a median tumor weight of 0.68 g which was not significantly different from the 5-FU/Leucovorin/DT-treated group ($p=0.27$). The combination of 25 mg/kg 5-FU/Leucovorin and DT immunization resulted in a median tumor weight of 0.96 g compared to a mean tumor weight of 0.68g in the anti-G17(1-9)-DT-immunized in conjunction with 5-FU/Leucovorin combination therapy group which was not significant ($p=0.409$). When the 5-FU/Leucovorin dose was reduced to 20 mg/kg, the 5-FU/Leucovorin/DT immunogen combination resulted in a median tumor weight of 1.23 g. The median tumor weight was significantly reduced to 0.71 g when 20 mg/kg of 5FU/leucovorin was combined with anti-G17(19)-DT immunization ($p=0.027$, Mann Whitney).

Finally, FIG. 5 also shows that a 5-FU/Leucovorin dose of 12.5 mg/kg combined with anti-G17(1-9)-DT immunization ($p=0.015$, Mann Whitney) reduces the median tumor weight from 1.34 g to 0.41 g. 5-FU/Leucovorin-anti-G17(1-9)-DT combinations were compared and no statistically significant difference existed between anti-G17(1-9)-DT given in combination with either 12.5, 20 or 30 mg/kg of 5-FU/Leucovorin.

Due to the limited benefit shown for combination chemotherapy with 5-FU/Leucovorin in both an advanced cancer state and, in particular, with an adjuvant therapy treatment setting (Moertel, 1994; Scheithauer, 1995; Taylor, 1993; Petrioli, 1995), new therapeutic modalities may need to be given either in conjunction with 5-FU/Leucovorin to enhance the therapeutic index (and possibly reduce the chemotherapeutic dose to limit toxicity) or as a second line treatment if chemotherapy fails to be effective. Thus new treatments must be amenable for such use. Immunotherapeutic approaches in conjunction with chemotherapy were previously thought to be problematic due to the myelosuppression associated with chemotherapeutic agents, such as that seen with 5-FU/Leucovorin (Mahood, 1991). In the present study, however, myelosuppression of rats induced with 5-FU/Leucovorin combinations of 30 mg/kg, administered according to Asao et al. at the maximum tolerated dose, did not affect the level of and time to achieve anti-ratG17:DT antibody titers following immunization with the anti-G17(1-9)-DT immunogen. In therapy studies using 5-FU/Leucovorin in combination with anti-G17(1-9)-DT, a potentiation of the 20 mg/kg and 12.5 mg/kg dosages was achieved. The 20 mg/kg dose was as effective as the maximum tolerated dose when combined with anti-G17(1-9)-DT, and the 12.5 mg/kg dose showed a trend to a greater therapeutic effect. The reason for the latter trend is not known but it may be due to the cytotoxic dose affecting the immune system to a lesser degree than higher dose levels, which may aid in the general inflammatory response against the tumor. 5FU/Leucovorin given in continuous cycles would appear to exert an 'all or nothing' effect on tumor growth as lowering the dose to 1 mg/kg was found to exert no inhibition of tumor growth. The therapeutic effect may be titrated out more gradually by reducing the number of toxic cycles (Watson, personal communication). Therefore, in the combinations according to the present invention, lower than usual doses of 5-FU/Leucovorin can be administered, thus reducing the side effects of the drugs, while, at the same time, effective killing of tumor cells can be achieved using the present combination, since the immune system is only minimally affected. Thus, the growth inhibitory effect of anti-G17(1-9)-DT immunization is enhanced. These characteristics of the combination therapy are unexpected and surprising in view of the myelosuppressive effects of the chemotherapeutic agents by themselves.

Furthermore, by the absence of deleterious effects on the host, anti-G17(1-9)-DT immunization is likely to be a long-term treatment as shown by the length of time that measurable antibody levels were present in rats receiving a single immunization. The first immunization was shown to be 80% effective, in terms of anti-gastrin antibody induction, and 100% effective after the second immunization with an immediate rise in antibody levels. Although potentiation of chemotherapy may be achieved by a single anti-G17(1-9)-DT injection, in most hosts the absence of side effects, characteristic of anti-G17(1-9)-DT immunization, and the host response rate following boosts, indicate a multi-injection regime may be desirable. Despite the length of time that anti-rat-G17 antibodies remained in the circulation there appeared to be no long term deleterious effects on the GI tract, as determined by a simple histological assessment. Additionally, the crypt cell proliferation index of mucosal cells in the colon revealed no significant effect on their growth.

EXAMPLE 6

Treatment of Human Colon Cancer Patients with a Combination Therapy of 5-FU/Leucovorin and Anti-G17 (l-9)-DT.

Anti-G17(1-9)-DT immunization alone has previously been shown to be a valuable and safe therapeutic option in the treatment of gastrin-dependent cancer. The present combinations of anti-G17 immunogens with 5-FU/Leucovorin enhance the effectiveness of cancer treatment, in particular colon cancer treatment, and the possible reduction in the dosage of the chemotherapeutic agent required in the combination should reduce the deleterious cytotoxic side effects of any of the chemotherapeutic agents now in use. The present combinations of an immunogen with chemotherapeutic agents may also be useful as a second-line therapy in patients who do not respond to chemotherapy alone.

Human colorectal tumor or colon cancer patients are treated with a combination of chemotherapy and immunotherapy.

Specifically, for patients with gastrin responsive colorectal tumors or colon cancer can be treated with concomitant administration of 5-FU/Leucovorin and an anti-G17 immunogen composition or anti-G17 antibodies.

In particular, the preferred immunotherapy provides an immunogenic composition comprising an aminoterminal G17 (1-9) peptide: DT conjugate in a pharmaceutically acceptable carrier which may include an adjuvant to further stimulate the immune response.

The preferred immunotherapeutic regimen can start before, during or after the chemotherapy course depending on clinical considerations. For example, in a patient with a large tumor burden it may be advantageous to start with several cycles of chemotherapy to reduce the tumor bulk and then start with immunotherapy.

Alternatively, in a patient with a small tumor burden or after curative surgery, immunotherapy can be started before or during chemotherapy.

The active immunization dose can range between 300 μg up to 1200 μg of the anti-G17 immunogen, depending on the immune status of the patient (or the capacity of an immune response). The injection intervals can be on days 1, 7 and 14, or days 1, 14 and 21, or days 1, 14, then 28 and 56. All the schedules can result in similar antibody titers. The accelerated schedules of immunization provide the possibility of earlier-onset of immune response.

The preferred method of the anti-gastrin therapy provides that a booster is administered every 6 months after the initial immunization period, regardless of which protocol is used.

Yet another preferred method for the effective neutralization of G17, Gly G17 and G17 $NH_2$ provides passive immunization with anti-G17 antibodies, preferably in purified form. More specifically, the inoculation of 10-1000 μg anti-G17 (1-9) antibodies is administered before, during and/or after the chemotherapy cycles-for the control of gastrin activities. The passive immunization can be administered daily, weekly or biweekly. Other protocols can be followed depending on the effectiveness of the treatment.

A further combination of treatment provides for an initial passive immunization before and/or during the first cycle of chemotherapy followed by active immunization as described above.

Many chemotherapy regimens are in use. These art recognized regimens, although not described herein, are not excluded from the combination treatment according to this invention. One preferred chemotherapy regimen provides for 5-FU i.v. bolus of 425 mg/m$^2$ with i.v. infusion of Leucovorin (folic acid, FA, 20 mg/m$^2$) for 1-5 days per period up to 4 weeks.

Another preferred regimen provides for 200 mg/m$^2$ FA over a period of 2 h, followed by 5-FU i.v. boles of 400 mg/m$^2$ +5-FU of 600 mg/m$^2$ over 22 hours 1 or 2 days in a 2-week period.

Yet another preferred regimen provides for continuous infusion of 5-FU at 250-300 mg/m$^2$ day continuous i.v. for 4-6 weeks, followed by 2 weeks rest.

REFERENCES

ASAO T, TAKAYUKI, SHIBATA H R, BATIST G and BRODT P. Eradication of Hepatic Metastases of Carcinoma H-59 combination chemoimmunotherapy with Liposomal Muramyl Tripeptide, 5-Fluorouracil, and Leucovorin. *Cancer Research* 52: 6254-6257, 1992

BALDWIN G. Binding of the progastrin fragments to the 78kDa gastrin-binding protein. *FEBS Lett* 1995; 359: 97-100.

ERLICHMAN C, FINE S, WONG A, ELHAKEIM T. A randomized trial of fluorouracil and folinic acid in patients with metastatic CRC. *J Clin Oncol* 1988; 6: 496-475.

MAHOOD D J, DOSE A M, LOPNIZ C C. Inhibition of Fluorouracil stomatitis by oral cryotherapy. *J Clin Oncol* 1991; 9: 449-452.

MAKISHIMA R, LARKIN D, MICHAELI D, GAGINELLA T S. Active immunization against gastrin-17 with an N-terminal derived immunogen inhibits gastrin and duodenal lesions in rats. *Gastroenterol* 1995; 106: A824.

MARTIN F, CAIGNARD A, JEANNIN J F, LECLERC A, MARTIN M. Selection of trypsin of 2 sublines of rat colon cancer cells forming progressive or regressive tumors. *Int J Cancer* 1983; 32: 623-627.

MOERTEL G G. Chemotherapy CRC. *NEJM* 1994; 330: 1136-1142.

PETRIOLI R, LORENZI M, AQUINO A, MARSILI S, FREDIANI B, PALAZZUOLI V, MARZOCCA G. Treatment of advanced colorectal cancer with high-dose intensity folinic acid and 5-Fluorouracil plus supportive care. *Eur J Cancer* 1995; 31A: 2105-2108.

PIETNELLI N, DOUGLAS H O, HARRAVA L. The modulation of Fluorouracil with leucovorin in metastatic CRC: a prospective randomized phase III trial. *J Clin Oncol* 1989; 7: 1419-1426.

SCHEITHAUER W, KORNEK G, ROSENH, SEBESTA C, MARCELL A, KWASNY W, KARALL M, DEPISCH D. Combined intraperitoneal plus intravenous chemotherapy after curative resection for colonic adenocarcinoma. *Eur J Cancer* 1995; 31A: 1981-1986.

SEVA C, DICKINSON C J, SAWADAM, YAMADA T. Characterization of the glycine-extended gastrin (G-gly) receptor on AR4-2J cells. *Gastroenterol* 1995; 108: A742.

TAYLOR, I. Chemotherapy, radiotherapy and immunology of colorectal neoplasia. *Current Opinion in Gastroenterology* 1993; 9: 28-33

WATSON S A and STEELE R J C. Gastrin receptors in gastrointestinal tumors. WG Landes Company, Austin, USA, 1993.

WATSON S A, MICHAELI D, GRIMES S, MORRIS T, ROBINSON G, VARRO A, JUSTIN T A, HARDCASTLE J D. Gastroimmune raises antibodies that neutralize amidated and glycine-extended gastrin-17 and inhibit the growth of colon cancer. Cancer Res 1996; 56: 880-885.

What is claimed is:

1. A combination of anti-gastrin-dependent tumor therapeutic ingredients, comprising:
   (i) an anti-gastrin G17 immunogen, wherein the anti-gastrin G17 immunogen comprises a peptide that has the sequence of amino acid residues pGlu-Gly-Pro-Trp-Leu-Glu-Glu-Glu-Glu as set forth in SEQ ID NO: 1; and
   (ii) one or more cytotoxic chemotherapeutic agents.

2. The combination of claim 1, wherein the anti-gastrin G17 immunogen comprises a therapeutically effective amount of the peptide.

3. The combination of claim 2, wherein the anti-gastrin G17 immunogen is conjugated to a Diphtheria toxoid.

4. The combination of claim 2, wherein the anti-gastrin G17 immunogen comprises the peptide that has the sequence of amino acid residues as set forth in SEQ ID NO: 1, a protein carrier, and a spacer peptide that links the peptide that has the sequence of amino acid residues as set forth in SEQ ID NO: 1 to the carrier.

5. The combination of claim 2, wherein the one or more cytotoxic chemotherapeutic agents are selected from the group consisting of 5-fluorouracil, leucovorin, levamisole, cisplatin, tumor necrosis factor, and proglumide.

6. The combination of claim 1, wherein each of the anti-gastrin G17 immunogen and the one or more cytotoxic chemotherapeutic agents comprises a pharmaceutically acceptable carrier.

7. The combination of claim 1, wherein the anti-gastrin G17 immunogen and the one or more cytotoxic chemotherapeutic agents are in separate compositions.

8. The combination of claim 1, wherein the anti-gastrin G17 immunogen and the one or more cytotoxic chemotherapeutic agents are formulated in the same composition.

9. A method of treatment of a gastrin-dependent tumor, comprising administering to a patient in need thereof the components of the combination of claim 1 to thereby treat the gastrin-dependent tumor in the patient.

10. The method of claim 9, wherein the peptide is conjugated to a diphtheria toxoid carrier.

11. The method of claim 9, wherein the anti-gastrin G17 immunogen comprises the peptide, a protein carrier, and a spacer peptide that projects the peptide away from the protein carrier and enhances capacity of the peptide to bind lymphocyte receptors.

12. The method of claim 9, wherein the one or more cytotoxic chemotherapeutic agents are selected from the group consisting of 5-fluorouracil, leucovorin, levamisole, cisplatin, tumor necrosis factor, and proglumide.

13. The method of claim 9, wherein the cytotoxic chemotherapeutic agent is 5-fluorouracil or leucovorin.

14. The method of claim 13, wherein the anti-gastrin-17 immunogen is administered prior to administration of the one or more cytotoxic chemotherapeutic agents.

15. The method of claim 9, wherein the anti-gastrin-17 immunogen is administered prior to administration of the one or more chemotherapeutic agents.

16. The method of claim 9, wherein the one or more cytotoxic chemotherapeutic agents are administered in several cycles.

* * * * *